(12) United States Patent
Batinic-Haberle et al.

(10) Patent No.: US 7,807,825 B2
(45) Date of Patent: Oct. 5, 2010

(54) SUBSTITUTED PORPHYRINS

(75) Inventors: Ines Batinic-Haberle, Durham, NC (US); Irwin Fridovich, Durham, NC (US); Ivan Spasojevic, Durham, NC (US)

(73) Assignee: Duke University, Durham, NC (US)

( * ) Notice: Subject to any disclaimer, the term of this patent is extended or adjusted under 35 U.S.C. 154(b) by 132 days.

(21) Appl. No.: 10/588,332

(22) PCT Filed: Feb. 1, 2005

(86) PCT No.: PCT/US2005/002691
§ 371 (c)(1),
(2), (4) Date: Mar. 22, 2007

(87) PCT Pub. No.: WO2005/077269
PCT Pub. Date: Aug. 25, 2005

(65) Prior Publication Data
US 2008/0021007 A1 Jan. 24, 2008

Related U.S. Application Data

(60) Provisional application No. 60/542,331, filed on Feb. 9, 2004.

(51) Int. Cl.
*C07B 47/00* (2006.01)
*C07D 487/22* (2006.01)
(52) U.S. Cl. .................................................. 540/145
(58) Field of Classification Search ................ 540/145; 514/183, 410
See application file for complete search history.

(56) References Cited

U.S. PATENT DOCUMENTS 6,479,477 B1 * 11/2002 Crapo et al. ................ 514/183
6,544,975 B1 * 4/2003 Crapo et al. ................ 514/185

FOREIGN PATENT DOCUMENTS

CN 1450066 A 10/2003
JP 02 242860 A 9/1990
WO WO0075144 12/2000

OTHER PUBLICATIONS

Pinedo et al., "Translational Research . . . ", The Oncologist 2000; 5(suppl 1); 1-2. [www.TheOncologist.com].*
McMahon, G., "VEGF Receptor Signaling in Tumor Angiogenisis.", The Oncologist 2000; 5(suppl 1); 3-10. [www.TheOncologist.com].*
Hunt et al., "Amphiphilic peroxynitrite . . . ", Chemistry & Biology 1997, vol. 4 No. 11, pp. 845-858.*
Dancil et al., "Synthesis and Aggregation of Cationic Porphyrins" *J. Heterocyclic Chem.*, 34, 749-755 (1997).
Gong et al., "Preparation and Characterization of Porphyrin Nanoparticles" *J. Am. Chem. Soc.* 124, 14290-14291 (2002).
Hunt et al, "Amphiphilic Peroxynitrite Decomposition Catalysts in Liposomal Assemblies" *Chemistry and Biology.* 4:845-858 (Nov. 1997).
International Search Report and Written Opinion for International Application No. PCT/US2005/02691, May 10, 2005.
Woehrle D et al. Metal chelates of porphyrin derivatives as sensitizers in photooxidation of sulphur compounds and in photodynamic therapy of cancer. Izvestia Akademii Nauk SSR. Seria Himiceskaa, Moscow, Russia. Jan. 1, 1994; 12: 2071-2082.
Gong X et al. Preparation and characterization of porphyrin nanoparticles. J Am Chem Soc. 2002; 124: 14290-14291.
Gong X. Large substituent containing porphyrin derivative, its preparation and application as small molecular antioxidant. Chemical Abstracts Service, Columbus, Ohio. Oct. 22, 2003: 3 pp.
Supplementary European Search Report, EP 05712218.6, mailed May 19, 2010.

* cited by examiner

*Primary Examiner*—James O. Wilson
*Assistant Examiner*—Paul V. Ward
(74) *Attorney, Agent, or Firm*—Myers Bigel Sibley & Sajovec, P.A.

(57) ABSTRACT

To improve bioavailability of the catalytic metalloporphyrin-based SOD mimics Mn(III) 5,10,15,20-tetrakis[N-ethylpyridinium-2-yl]porphyrin (MnTE-2-PyP$^{5+}$) and Mn(III) 5,10,15,20-tetrakis[N,N'-diethylimidazolium-2-yl]porphyrin (MnTDE-2-ImP$^{5+}$), three new Mn(III) porphyrins, bearing oxygen atoms within side chains, were synthesized and characterized: Mn(III) 5,10,15,20-tetrakis[N-(2-methoxyethyl)pyridinium-2-yl]porphyrin (MnTMOE-2-PyP$^{5+}$), Mn(III) 5,10,15,20-tetrakis[N-methyl-N'-(2-methoxyethyl)imidazolium-2-yl]porphyrin (MnTM,MOE-2-ImP$^{5+}$) and Mn(III) 5,10,15,20-tetrakis[N,N'-di(2-methoxyethyl)imidazolium-2-yl]porphyrin (MnTDMOE-2-ImP$^{5+}$). The catalytic rate constants for $O_2$ dismutation (and the related metal-centered redox potentials vs NHE) for the new compounds are: log $k_{cat}$=8.04 ($E_{1/2}$=+251 mV) for MnTMOE-2-PyP$^{5+}$, log $k_{cat}$=7.98 ($E_{1/2}$=+356 mV) for MnTM,MOE-2-ImP$^{5+}$ and log $k_{cat}$=7.59 ($E_{1/2}$=+365 mV) for MnTDMOE-2-ImP$^{5+}$. At 30 μM levels none of the new compounds were toxic, and allowed SOD-deficient *E. coli* to grow nearly as well as wild type. At 3 μM levels, the MnTDMOE-2-ImP$^{5+}$, bearing an oxygen atom within each of the eight side chains, was the most effective and offered much higher protection than MnTE-2-PyP$^{5+}$, while MnTDE-2-ImP$^{5+}$ was inefficient. These new porphyrins were compared to Mn(III) N-alkylpyridylporphyrins. While longer-chain n-alkyl members of the series exerted toxicity at higher concentration levels, they were very effective at submicromolar levels. Thus, 0.3 μM Mn(III) tetrakis(N-n-hexyl-pyridinum-2-yl)porphyrin and its n-octyl analogue offered the same level of protection as did >10 μM methyl and ethyl porphyrins. The $k_{cat}$ of methyl and n-octyl porphyrins are identical, but n-octyl is −10-fold more lipophilic. Therefore, the 30-fold improvement in bioavailability appears to be due to the increase in lipophilicity. MnTDMOE-2-ImP$^{5+}$ and longer-chain Mn(III) N-alkylpyridylporphyrins may offer better treatment for oxidative stress injuries than the previously studied MnTE-2-PyP$^{5+}$ and MnTDE-2-ImP$^{5+}$.

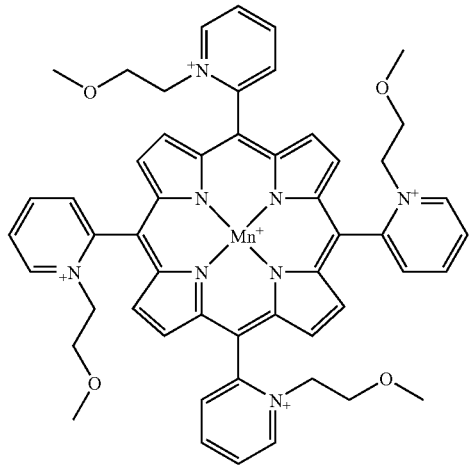
Mn<sup>III</sup>TMOE-2-PyP<sup>5+</sup>
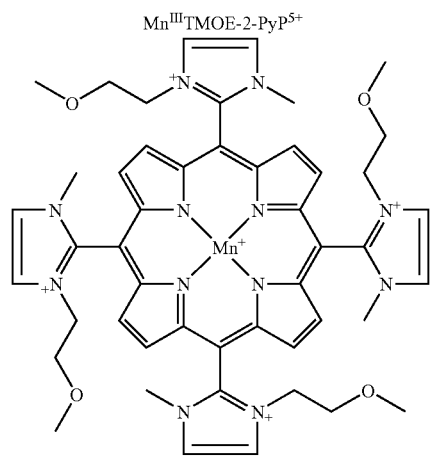
Mn<sup>III</sup>TM, MOE-2-Imp<sup>5+</sup>
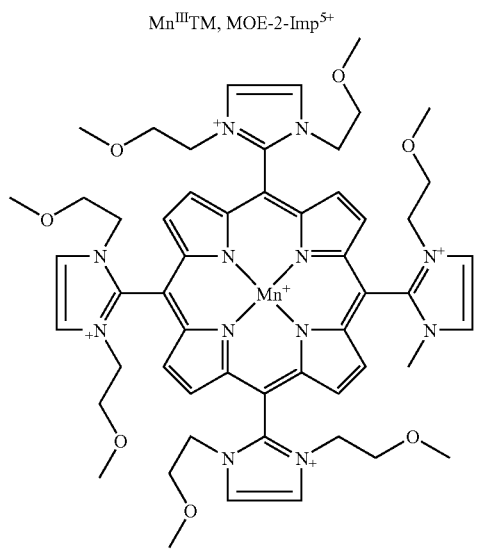
Mn<sup>III</sup>DMOE-2-Imp<sup>5+</sup>
-continued
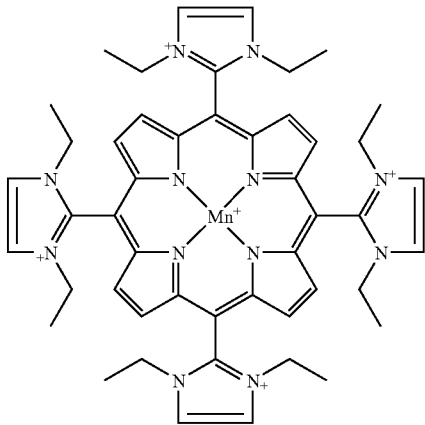
Mn<sup>III</sup>TDE-2-Imp<sup>5+</sup>
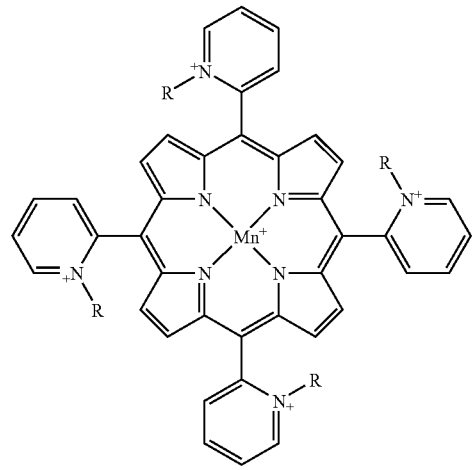
Mn<sup>III</sup>T(alkyl)-2-PyP<sup>5+</sup>
R = alkyl = methyl to n-octyl)
10 Claims, 10 Drawing Sheets

Structures of the Mn(III) porphyrins studied

US 7,807,825 B2

SUBSTITUTED PORPHYRINS

RELATED APPLICATIONS

The present application is a 35 U.S.C. §371 national phase application of PCT International Application No. PCT/US2005/002691, having an international filing date of Feb. 1, 2005, which claims the benefit, under 35 U.S.C. §119(e), of U.S. Provisional Application Ser. No. 60/542,331, filed Feb. 9, 2004, the entire contents of each of which are incorporated by reference herein.

TECHNICAL FIELD

The present invention relates generally to porphyrins and, more particularly to substituted porphyrins and to methods of using same.

BACKGROUND

Mn(III) cationic N-alkylpyridylporphyrin mimics of SOD activity have been developed (Spasojevic et al, J. Biol. Chem. 278:6831-6837 (2003), Batinic-Haberle, Methods Enzymol. 349:223-233 (2001), Spasojevic and Batinic-Haberle, Inorg. Chim. Acta. 317:230-242 (2001), Batinic-Haberle et al, J. Biol. Chem. 273:24521-24528 (1998), Batinic-Haberle et al, Inorg. Chem. 38:4011-4022 (1999), Kachadourian et al, Inorg. Chem. 38:391-396 (1999), Batinic-Haberle et al, J. Chem. Soc., Dalton Trans., pgs. 2689-2696 (2002), Ferrer-Sueta et al, J. Biol. Chem. 278:27432-27438 (2003)) the N-ethylpyridyl derivative of which, MnTE-2-PyP$^{5+}$ (Spasojevic et al, J. Biol. Chem. 278:6831-6837 (2003)), exhibits beneficial antioxidant properties in several animal models of oxidative stress injury (Tao et al. Circulation 108:2805-2811 (2003), Sheng et al, J. Neurotrauma, In press (2003), Sheng et al, Drug News and Perspectives 15:654-665 (2002), Sheng et al, Free Radic. Biol. Med. 33:947-961 (2002), Vujaskovic et al, Free Radic. Biol. Med. 33:857-863 (2002), Piganelli et al, Diabetes 51:347-355 (2002), Trostchansky et al, Free Radic. Biol. Med. 35:1293-1300 (2003), Mackensen et al, J. Neurosci. 21:4582-4592 (2001), Aslan et al, Proc. Natl. Acad. Sci. USA 98:15215-15220 (2001), Sheng et al, Free Radic. Biol. Med. In preparation (2003)). Based on the structure-activity relationship, that revealed the key roles of metal-centered redox potential (Batinic-Haberle et al, Inorg. Chem. 38:4011-4022 (1999)) and electrostatics (Spasojevic et al, J. Biol. Chem. 278:6831-6837 (2003)) on the superoxide ($O_2.^-$) dismuting ability, a similar compound, N,N'-diethylimidazolyl derivative, MnTDE-2-ImP$^{5+}$, was synthesized and was proven effective in vivo (Sheng et al, Drug News and Perspectives 15:654-665 (2002), Sheng et al, Free Radic. Biol. Med. 33:947-961 (2002), Sheng et al, Free Radic. Biol. Med. In preparation (2003), Bottino et al, Diabetes 51:2561-2567 (2002), Bowler et al, Free Radic. Biol. Med. 33:1141-1152 (2002)). Besides dismuting $O_2.^-$, Mn(III) ortho N-alkylpyridylporphyrins are able to efficiently scavenge peroxynitrite (k>$10^7 M^{-1} s^{-1}$) (Ferrer-Sueta et al, J. Biol. Chem. 278:27432-27438 (2003), Ferrer-Sueta et al, Chem. Res. Toxicol. 12:442-449 (1999)) and carbonate radical (k>$10^8 M^{-1} s^{-1}$) (Ferrer-Sueta et al, J. Biol. Chem. 278:27432-27438 (2003)). In addition, these Mn porphyrins undergo reductive nitrosylation with NO. (Spasojevic et al, Nitric Oxide: Biology and Chemistry 4:526-533 (2000)). Finally, they are readily reduced by cellular reductants such as ascorbic acid (Batinic-Haberle et al, J. Chem. Soc., Dalton Trans., pgs. 2689-2696 (2002), Ferrer-Sueta et al, Chem. Res. Toxicol. 12:442-449 (1999), Spasojevic et al, Nitric Oxide: Biology and Chemistry 4:526-533 (2000), Bloodsworth et al, Free Radic. Biol. Med. 28:1017-1029 (2000)), glutathione (Spasojevic et al, Nitric Oxide: Biology and Chemistry 4:526-533 (2000)), tetrahydrobiopterin (Spasojevic and Fridovich, Free Radic. Biol. Med. 33(Suppl. 2):S316 (2002)), and uric acid (Trostchansky et al, Free Radic. Biol. Med. 35:1293-1300 (2003), Ferrer-Sueta et al, Chem. Res. Toxicol. 12:442-449 (1999)). Thus, the catalytic elimination of $O_2.^-$, ONOO$^-$, and $CO_3.^-$ by Mn porphyrins is likely made possible in vivo through coupling with cellular reductants. Through modulation of the levels of reactive oxygen (ROS) and nitrogen (RNS) species, Mn porphyrins can favorably affect cellular redox status and redox sensitive signaling processes (Mikkelsen and Wardman, Oncogene 22:5734-5754 (2003), Chen et al, Free Radic. Biol. Med. 35:117-132 (2003)).

In vivo studies (Trostchansky et al, Free Radic. Biol. Med. 35:1293-1300 (2003), Sheng et al, Free Radic. Biol. Med. In preparation (2003)) indicated that the efficacy of Mn porphyrins can be improved by increasing their lipophilicity. Hence, a series of ortho N-alkylpyridylporphyrins were prepared, wherein the length of N-pyridyl alkyls was increased from methyl to n-octyl (Batinic-Haberle et al, S. Chem. Soc., Dalton Trans., pgs. 2689-2696 (2002)). While all Mn porphyrins of the series can scavenge $O_2.^-$ (Batinic-Haberle et al, J. Chem. Soc., Dalton Trans., pgs. 2689-2696 (2002)) and ONOO$^-$ (Ferrer-Sueta et al, J. Biol. Chem. 278:27432-27438 (2003)) with nearly equal effectiveness, their in vivo performance differs greatly. An increase in the length of the alkyl chains increases lipophilicity up to 10-fold (Batinic-Haberle et al, J. Chem. Soc., Dalton Trans., pgs. 2689-2696 (2002)). Consequently, their bioavailability can be expected to increase as well. However, as the alkyl chains lengthen, the surfactant character of the porphyrin increases, leading to the potential for increased toxicity. At higher concentrations this effect may predominate over any gain in activity resulting from increased bioavailibility. An attempt was made to overcome the toxicity by working at low concentrations where the sole impact of lipophilicity would be assessed.

The present invention results from studies involving modification of the ortho N-alkylpyridyl and di-ortho N,N'-dialkylimidazolyl chains by introducing ether oxygen. 2-Methoxyethyl analogues of MnTE-2-PyP$^{5+}$ (FIG. 1, MnTMOE-2-PyP$^{5+}$) and of MnTDE-2-ImP$^{5+}$ (FIG. 1, MnTDMOE-2-ImP$^{5+}$) were synthesized. When compared to ortho pyridylporphyrins, di-ortho imidazolyl compounds have both imidazolyl nitrogens substituted with ethyl(methyl) or methoxyethyl groups. The ortho N-alkylpyridylporphyrins exist as a mixture of positional (atropo-)isomers (Spasojevic et al, Inorg. Chem. 41:5874-5881 (2002)), whereas di-ortho imidazolyl compounds with eight identical imidazolyl substituents do not have positional isomers. As described in the Example that follows, the potency and toxicity of the new Mn porphyrins were assessed using the SOD-deficient E. coli model of oxidative stress (Batinic-Haberle et al, J. Biol. Chem. 273:24521-24528 (1998), Batinic-Haberle et al, Inorg. Chem. 38:4011-4022 (1999)) which has been proven useful in the past in evaluating prospective candidates for animal models of oxidative stress injuries.

DETAILED DESCRIPTION OF THE INVENTION

Figure 1:
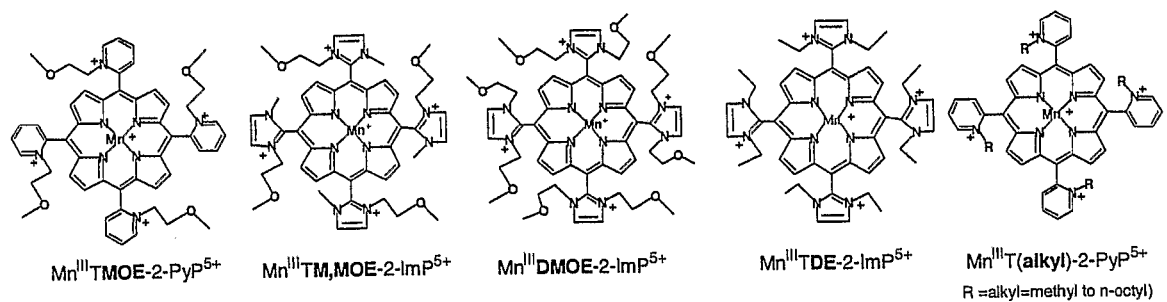
FIG. 1. Structures of the Mn(III) porphyrins studied.

The present invention relates to a compound of Formula:

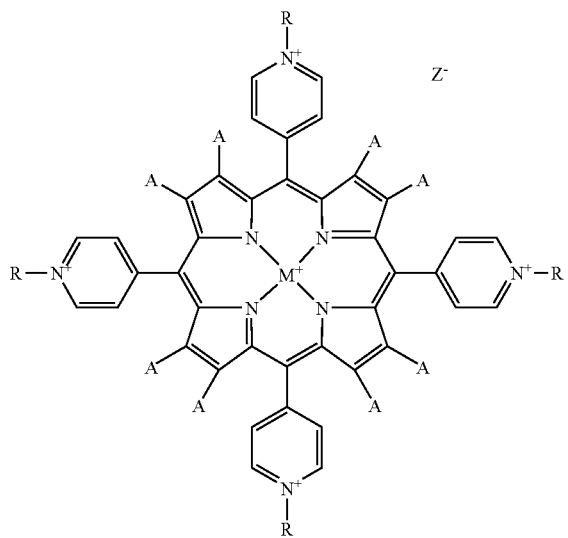

I

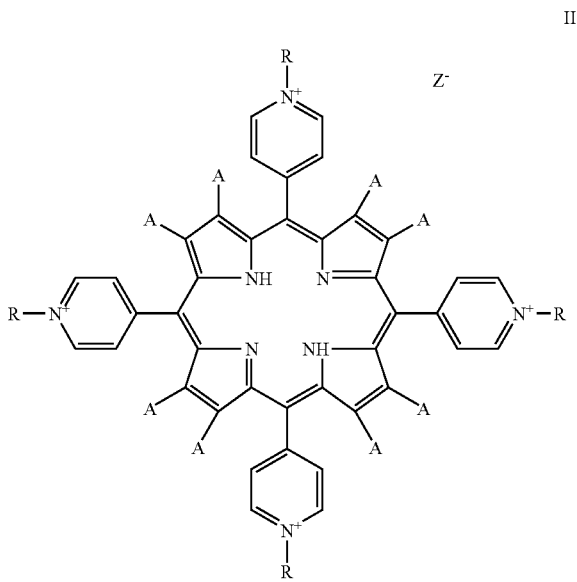

II

-continued

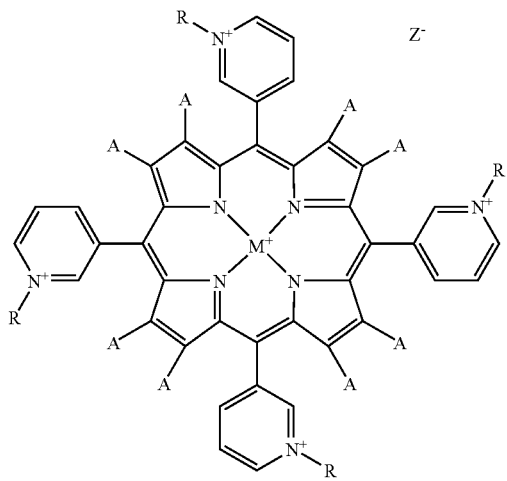

III

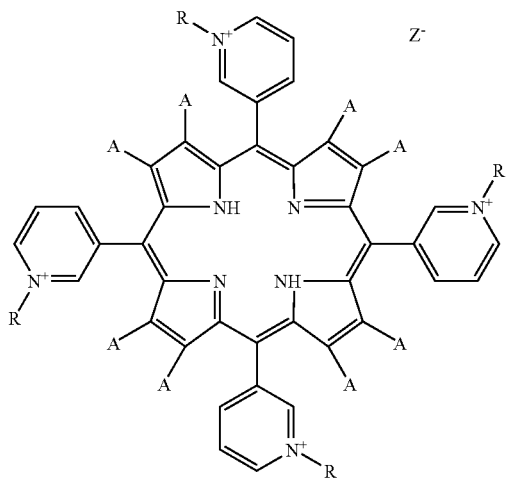

IV

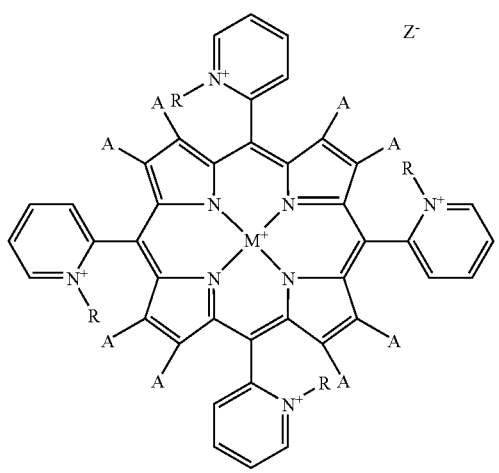

V

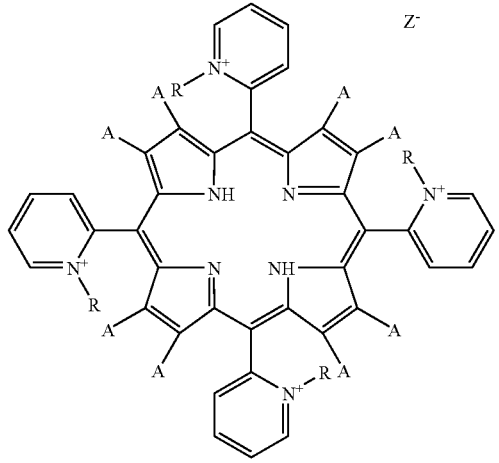

VI

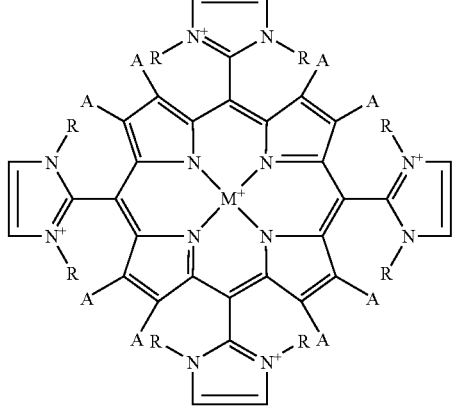

VII

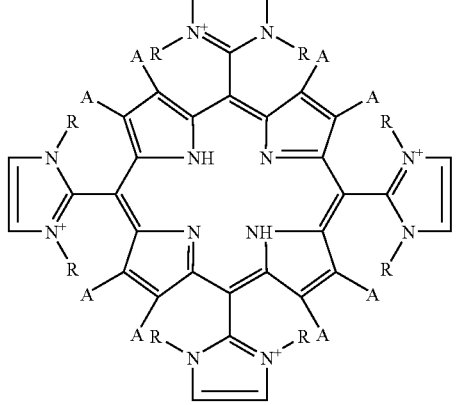

VIII

When the compound is of Formula I-VI, each R is, independently, —(CH$_2$)$_m$CH$_2$OX or —(CH$_2$CH$_2$O)$_n$X, wherein m is 1-6, preferably 1-4, more preferably 1 or 2;
n is 3-50, preferably 3-10, more preferably 3, 4 or 5;
X is C$_{1-12}$alkyl (straight chain or branched), preferably C$_{1-8}$alkyl, more preferably C$_{1-4}$alkyl. Each R can be the same.

When the compound is of Formula VII or VIII, at least one R on each imidazole ring is, independently, —(CH$_2$)$_m$CH$_2$OX or —(CH$_2$CH$_2$O)$_n$X, the other R being, independently, a $C_1$-$C_{12}$alkyl, (straight chain or branched), preferably a $C_{1-8}$alkyl, more preferably a $C_1$, $C_2$, $C_3$ or $C_4$ alkyl;

wherein m is 1-6, preferably 1-4, more preferably 1 or 2;

n is 3-50, preferably 3-10, more preferably 3, 4 or 5;

X is $C_{1-12}$alkyl (straight chain or branched), preferably $C_{1-8}$alkyl, more preferably $C_{1-4}$alkyl. Advantageously, each R is the same and is —$(CH_2)_nCH_2OX$.

When the compound is any of Formulas I-VIII, each A is, independently, hydrogen or an electron withdrawing group, for example, a halogen (e.g., Cl, Br or F), $NO_2$, or CHO, preferably each A is hydrogen or halogen, more preferably at least one A is halogen and the remaining A's are hydrogen, still more preferably 1-4 A's are, independently, Cl or Br and the remaining A's are hydrogen. M is metal selected from the group consisting of manganese, iron, copper, cobalt, nickel and zinc (preferably manganese). $Z^-$ is a counterion (e.g., chloride).

To the extent that Hunt et al, Chem. Biol. 4:846-858 (1997), Szabó et al, Mol. Med. 8:571-580 (2002), and/or Mabley et al, Mol. Med. 8:581-590 (2002) may describe compounds within the scope of the definitions set forth above, those specific compounds are outside the scope of the compound per se and/or method embodiments of the present invention.

The invention further relates to a method of protecting cells (eg mammalian cells) from oxidant-induced toxicity comprising contacting the cells with a protective amount of a compound as described above. The invention further relates to a method of treating a pathological condition of a patient resulting from oxidant-induced toxicity comprising administering to the patient an effective amount of such a compound. The invention also relates to a method of treating a pathological condition of a patient resulting from degradation of NO., comprising administering to the patient an effective amount of a compound as described above. Additionally, the invention relates to a method of treating a patient for inflammatory lung disease comprising administration to the patient an effective amount of a compound as described above. The inflammatory lung disease can be a hyper-reactive airway disease. The disease can be asthma.

Additionally the invention relates to a method of treating a neurodegenerative condition of a patient comprising administering to the patient an effective amount of a compound as described above. Neurodegenerative disease can be familial amyotrophic lateral sclerosis, Parkinson disease, Picks disease, Alzheimers, spinal cord injury, stroke, multiple sclerosis, Mad cow disease, Jacob-Creutzfeld disease.

Additionally the invention relates to a method of treating radiation injury and cancer of a patient comprising administering to the patient an effective amount of a compound as described above.

Additionally the invention relates to a method of treating a diabetic condition of a patient comprising administering to the patient an effective amount of a compound as described above.

Additionally the invention relates to a method of treating a cardiac condition of a patient comprising administering to the patient an effective amount of a compound as described above.

Additionally the invention relates to a method of treating a sickle cell disease condition of a patient comprising administering to the patient an effective amount of a compound as described above.

The compounds disclosed herein can be used in the treatment of the diseases, disorders and conditions described in U.S. Pat. No. 5,994,339, U.S. Pat. No. 6,127,356, U.S. Pat. No. 6,479,477, WO 99/23097, U.S. Pat. No. 6,544,975, WO 01/96345, WO 02/060383 and PCT/US02/17144.

The compounds described above, metal bound and metal free forms, can be formulated into pharmaceutical compositions suitable for use in the present methods. Such compositions include the compound(s) (active agent) together with a pharmaceutically acceptable carrier, excipient or diluent. The composition can be present in dosage unit form, for example, tablets, capsules or suppositories. The composition can also be in the form of a sterile solution suitable for injection or nebulization. Compositions can also be in a form suitable for opthalmic use. The invention also includes compositions formulated for topical administration, such compositions taking the form, for example, of a lotion, cream, gel or ointment. The concentration of active agent to be included in the composition can be selected based on the nature of the agent, the dosage regimen and the result sought.

The dosage of the composition of the invention to be administered can be determined without undue experimentation and will be dependent upon various factors including the nature of the active agent (including whether metal bound or metal free), the route of administration, the patient, and the result sought to be achieved. A suitable dosage to be administered IV or topically can be expected to be in the range of about 0.01 to 50 mg/kg/day, preferably, 0.1 to 10 mg/kg/day. For aerosol administration, it is expected that doses will be in the range of 0.001 to 5.0 mg/kg/day, preferably, 0.01 to 1 mg/kg/day. Suitable doses will vary, for example, with the compound and with the result sought.

Certain aspects of the present invention will be described in greater detail in the non-limiting Example that follow.

Example

Experimental Details

General. $MnCl_2 \times 4H_2O$, and Baker-flex silica gel IB TLC plates were purchased from J.T. Baker. N,N-dimethylformamide, 2-propanol (99.5+%), $NH_4PF_6$ (99.99%), NaCl, sodium L-ascorbate, and tetrabutylammonium chloride were from Aldrich, while xanthine, $K_2CO_3$, albumin, bovine (# C-3131) and equine ferricytochrome c (lot # 7752) were from Sigma. The ethyl(n-butyl) p-toluenesulfonate and methoxyethyl p-toluenesulfonate were from TCI America. Acetone, ethyl ether (anhydrous), chloroform, NaCl, KOH, $KH_2PO_4$, methanol, EDTA and $KNO_3$ were from Mallinckrodt and acetonitrile was from Fisher Scientific. Tris (ultra pure) was from ICN Biomedicals, Inc. Xanthine oxidase was prepared by R. Wiley and was supplied by K. V. Rajagopalan (Waud et al, Arch. Biochem. Biophys. 19:695-701 (1975)). Catalase was from Boehringer, and ultrapure argon from National Welders Supply Co.

Mn(III) Porphyrins. Synthesis. The $H_2$T-2-PyP, $H_2$TM-2-ImP and $H_2$T-2-ImP were supplied from MidCentury Chemicals (Chicago, Ill.). The N-ethylation, N-butylation and N-methoxyethylation of $H_2$T-2-PyP and N-methoxyethylation of $H_2$TM-2-ImP were accomplished as previously described (Batinic-Haberle, Methods Enzymol. 349:223-233 (2001), Batinic-Haberle et al, J. Biol. Chem. 273:24521-24528 (1998)). However, the method proved unsuccessful when N,N'-dimethoxyethylation of $H_2$T-2-ImP was attempted to prepare $H_2$TDMOE-2-ImP$^{4+}$. Thus, no single fully quaternized product was obtained. In this case, N,N'-methoxyethylation was conducted under alkaline/anhydrous conditions to facilitate the proton release (Milgrom et al, Tegrahedron 52:9877-9890 (1996)). Thus, 30 mg of $H_2$T-2-ImP in 7 mL of DMF was purged with argon, then 300 mg of $K_2CO_3$ was added followed by the addition of 7 mL of methoxyethyl p-toluene sulfonate (higher amount of $K_2CO_3$ will lead to the formation of undesired products). The quaternization was followed by thin-layer chromatography on silica gel plates with $KNO_3satH_2O/H_2O$/acetonitrile=1/1/8. The isolation of the chloride salt was performed as previously described (Batinic-Haberle et al, J. Biol. Chem. 273:24521-24528 (1998), Batinic-Haberle et al, Inorg. Chem. 38:4011-4022 (1999)). As was the case with longer N-alkylpyridylporphyrins, diethyl ether alone instead of diethyl ether/2-propanol, 1/1, was used to rinse the $PF_6^-$ salt. The same conditions were then applied for N,N'-diethylation of $H_2T$-2-ImP. Insertion of manganese into the porphyrin ligand was achieved as previously described for N-alkylpyridylporphyrins. The formation of Mn(II) porphyrin occurs readily. The oxidation of manganese was most rapid with N-methoxyethylpyridylporphyrin and the slowest (within an hour) with N,N'-dimethoxyethylimidazolylporphyrin. The purification and isolation of Mn complexes was the same as with their respective ligands. Elemental analysis: $H_2$TMOE-2-$PyPCl_4 \times 9 H_2O$ ($C_{52}H_{72}N_8O_{13}Cl_4$): Found: C, 53.93; H, 6.09; N, 10.05; Cl, 12.73. Calculated: C, 53.89; H, 6.26; N, 9.67; Cl, 12.24. MnTMOE-2-$PyPCl_5 \times 9$ $H_2O$ ($C_{52}H_{70}N_8O_{13}MnCl_5$): Found: C, 49.97; H, 4.83; N, 10.32; Cl, 14.77. Calculated: C, 50.07; H, 5.65; N, 8.98; Cl, 14.21. $H_2$TM,MOE-2-$ImPCl_4 \times 12.5$ $H_2O \times 1.5$ $NH_4Cl$ ($C_{48}H_{89}N_{12}O_{16.5}Cl_{5.5}$): Found: C, 43.70; H, 6.25; N, 13.99; Cl, 14.74. Calculated: C, 43.87; H, 6.82; N, 14.38; Cl, 14.84. MnTM,MOE-2-$ImPCl_5 \times 12.5$ $H_2O \times 0.5$ $NH_4Cl$ ($C_{48}H_{81}N_{12}O_{16.5}MnCl_{5.5}$): Found: C, 42.64; H, 5.70; N, 13.07; Cl, 14.11. Calculated: C, 42.73; H, 6.19; N, 12.98; Cl, 14.45. $H_2$TDMOE-2-$PyPCl_4 \times 8$ $H_2O$ ($C_{56}H_{90}N_{12}O_{24}Cl_4$). Found: C, 50.73; H, 6.56; N, 12.74; Cl, 11.73. Calculated: C, 50.60; H, 6.82; N, 12.64; Cl, 10.67. MnTDMOE-2-$PyPCl_5 \times$ 12.5 $H_2O$ ($C_{56}H_{97}N_{12}O_{20.5}MnCl_5$). Found: C, 44.78; H, 6.18; N, 11.40; Cl, 11.95. Calculated: C, 44.88; H, 6.52; N, 11.21; Cl, 11.82. $H_2$TDE-2-$ImPCl_4 \times 8.5$ $H_2O$ ($C_{48}H_{75}N_{12}O_{8.5}Cl_4$). Found: C, 52.57; H, 6.86; N, 15.27; Cl, 12.66. Calculated: C, 52.50; H, 6.88; N, 15.31; Cl, 12.91. MnTDE-2-$ImPCl_5 \times 14$ $H_2O$ ($C_{48}H_{84}N_{12}O_{14}Cl_5Mn$). Found: C, 44.78; H, 6.51; N, 13.11; Cl, 13.60. Calculated: C, 44.85; H, 6.58; N, 13.08; Cl, 13.79.

Uv/vis spectra of porphyrin ligands and their Mn complexes were taken on a Shimadzu UV-2501-PC spectrophotometer at 25° C. Thin-layer chromatography of ligands and Mn complexes was done using silica gel plates with $KNO_3satH_2O/H_2O$/acetonitrile=1/1/8.

Electrochemistry. Measurements were performed on a CH Instruments Model 600 Voltammetric Analyzer (Spasojevic and Batinic-Haberle, Inorg. Chim. Acta. 317:230-242 (2001), Batinic-Haberle et al, J. Biol. Chem. 273:24521-24528 (1998), Batinic-Haberle et al, Inorg. Chem. 38:4011-4022 (1999)). A three-electrode system in a small volume cell (0.5 mL to 3 mL), with a 3 mm-diameter glassy carbon button working electrode (Bioanalytical Systems), plus the Ag/AgCl reference and Pt auxilliary electrodes was used. Argon-purged solutions contained 0.05 M phosphate buffer, pH 7.8, 0.1 M NaCl, and 0.5 mM metalloporphyrin. The scan rates were 0.01-0.5 V/s, typically 0.1 V/s. The potentials were standardized against the potassium ferrocyanide/ferricyanide (Kolthof and Tomsicek, J. Phys. Chem. 39:945 (1935)) and/or against MnTE-2-$PyP^{5+}$ (Spasojevic and Batinic-Haberle, Inorg. Chim. Acta. 317:230-242 (2001), Batinic-Haberle et al, J. Biol. Chem. 273:24521-24528 (1998), Batinic-Haberle et al, Inorg. Chem. 38:4011-4022 (1999)).

Electrospray mass spectrometry. ESMS measurements were performed on a Micromass Quattro LC triple quadrupole mass spectrometer equipped with a pneumatically assisted electrostatic ion source operating at atmospheric pressure as previously described (Batinic-Haberle et al, J. Porphyrins Phthalocyanines 4:217-227 (2000)). Typically, the 0.5 mM 50% aqueous acetonitrile solutions of chloride salts of metal-free porphyrins or their Mn(III) complexes were introduced by loop injection into a stream of 50% aqueous acetonitrile flowing at 8 μL/min. Mass spectra were acquired in continuum mode, scanning from 100-500 m/z in 5 s, with cone voltages of 20 V and 30 V. The mass scale was calibrated using polyethylene glycol.

Catalysis of $O_2.^-$ dismutation. The catalytic rate constants for the $O_2.^-$ dismutation were determined by pulse radiolysis in 0.05 M phosphate buffer (pH 7.8) at $(22\pm1)°$ C. as previously described (Batinic-Haberle et al, Inorg. Chem. 40:726 (2001)). In the present study 10 mM formate was used as a scavenger for H. atoms and .OH radicals, which leads first to production of $CO_2.^-$) radicals and then to $O_2.^-$ radicals. This system is known to lead to conversion of all primary radicals of water radiolysis into $O_2.^-$.

The pulse radiolysis was used as an alternative method to cytochrome c assay in order to circumvent problems encountered with different cytochrome c preparations. Namely, the $k_{cat}$ values of each porphyrin, determined by cytochrome c assay (McCord and Fridovich, J. Biol. Chem. 244:6049 (1969)), varied from 0.1 to 0.5 log units depending upon the particular cytochrome c preparation used. Sigma-Fluka product #2327009 (#30396) previously used is no longer available (Batinic-Haberle et al, Anal. Biochem. 275:267 (1999)). Problems experienced with Sigma cytochrome c #2506 for studying positively charged Mn porphyrins have been reported (Batinic-Haberle et al, Anal. Biochem. 275:267 (1999)). Similar problems were encountered with cytochrome c #3131. In comparative studies, however, the cytochrome c assay was still used because of its simplicity and product #7752 has been found the best for this purpose among those presently offered by Sigma.

Kinetic salt effect. The dependence of the catalytic rate constant for the $O_2.^-$ dismutation upon ionic strength was determined by cytochrome c assay (McCord and Fridovich, J. Biol. Chem. 244:6049 (1969)) in 0.05 M phosphate buffer, pH 7.8 with NaCl ranging from 0 to 0.4 M. In doing this, the effect of ionic strength on the rate of the $O_2.^-$/cytochrome c reaction was corrected for.

Aerobic growth of E. coli. Bacterial strains of E. coli used were wild type AB 1157 (F-thr-I leu-1 proA2 his-4 argE3 thr-1 lacY1 galK2 rpsL supE44 ara-14 xyl-15 mtl-1 tsx-33) and SOD-deficient JI132 (same as AB 1157 plus (sodA::mudPR13)25 (sodB-kan)1-Δ2. Culture media were prepared as follows. M9 medium: 6 g/L $Na_2HPO_4$, 3 g/L $KH_2PO_4$, 0.5 g/L NaCl, 1 g/L $NH_4Cl$, 2 mM $MgSO_4$, 0.1 mM $CaCl_2$, adjusted to pH 7.4 with NaOH, and supplemented with 0.2% glucose, 3 mg/L each of D-panthotenic acid and thiamine. M9CA medium contained M9 medium plus 0.2% casamino acids. 5-amino acid (5AA) minimal medium contained M9 medium plus 0.5 mM each of threonine, leucine, histidine, proline and arginine (Faulkner et al, J. Biocl. Chem. 269: 23471 (1994)).

AB1157 and JI132 were precultured overnight aerobically in M9CA medium at 37° C. and were then diluted to $3 \times 10^7$ cells/mL into 5 mL M9CA medium. JI132 was precultured in the presence of 20 μg/mL chloramphenicol and 500 μg/mL kanamycin. When the cells are transferred from M9CA medium to 5AA minimal medium cultures were first centrifuged and washed twice with the 5AA medium before final dilution in it. The centrifugation was conducted at room temperature to avoid temperature shocks. Cultures without and with Mn porphyrins (0.1 to 30 μM) were grown aerobically in 5 mL volume in test tubes in a thermostated orbital shaker (45° angle, 200 rpm) at 37° C.). Rates of growth were followed turbidimetrically at 700 nm to minimize interference from the absorbance of test compounds.

Catalysis of $O_2.^-$ dismutation in the presence of *E. coli* cell extract and albumin. The cytochrome c assay (McCord and Fridovich, J. Biol. Chem. 244:6049 (1969)) was used to test SOD-like activity in the presence and absence of *E. coli* cell extract. SOD-deficient *E. coli* (JI132, ΔsodA/ΔsodB) was used for cell extract preparations. Extracts were prepared from 6 hour-cultures which were washed twice in 0.05 M phosphate buffer, re-suspended in the buffer and disrupted with a French press. The lysate was clarified by centrifugation and the supernatant used for experiments. The SOD activity was examined with or without JI132 cell lysate. Before examination, the cell extracts containing 1, 10, or 100 μg/mL proteins were incubated for 4 hours at 4° C. with Mn porphyrins.

Thin-layer chromatography. The retention factors, $R_f$(porphyrin path/solvent path) for porphyrins ligands and their Mn complexes are given in Table 1. All new methoxyporphyrins are more lipophilic than MnTE-2-PyP$^{5+}$ and MnTDE-2-ImP$^{5+}$.

Uv/vis spectroscopy. The porphyrins obeyed the Beer-Lambert law from $10^{-7}$ M to $10^{-5}$ M, and the uv/vis data are given in Table 2. A red shift averaging 1-2 nm was generally observed as the result of the increased porphyrin nucleus distortion due to the enhanced crowding upon replacement of n-butyl with methoxyethyl groups. The red shift was accompanied by an increase in ∈ of up to 0.1 log unit. The Soret bands of di-ortho H$_2$TDE-2-ImP$^{4+}$ and its Mn complex are blue-shifted by 7 and 8 nm, respectively when compared to the mono ortho pyridyl analogues as a consequence of increased electron-withdrawing effect due to charge delocalization. This observation parallels the markedly increased metal-centered redox potential of imidazolylporphyrins vs pyridylporphyrins.

In the presence of ascorbic acid, at pH 7.8 (0.05 M tris buffer), under aerobic conditions, Mn(III) porphyrins are readily reduced. Under these conditions porphyrins underwent oxidative degradation. As previously observed (Batinic-Haberle et al, J. Chem. Soc., Dalton Trans., pgs. 2689-2696 (2002)), those porphyrins that are of more positive $E_{1/2}$ are stabilized in +2 oxidation state and are less prone to oxidative damage. Accordingly, 27% and 24% of MnTE-2-PyP$^{5+}$ and MnTMOE-2-PyP$^{5+}$ undergo degradation within 2 hours, but only 2% of MnTM,MOE-2-ImP$^{5+}$ and MnTDMOE-2-ImP$^{5+}$ and 3% of MnTDE-2-ImP$^{5+}$. The same level of stability was previously observed with n-hexyl and n-octyl porphyrins (Batinic-Haberle et al, J. Chem. Soc., Dalton Trans., pgs. 2689-2696 (2002)).

Electrochemistry. All cyclic voltammograms, ascribed to the Mn(III)/Mn(II) redox couple, are reversible. The metal-centered redox potentials, $E_{1/2}$ are listed in Table 1. The $E_{1/2}$ of di-ortho ethylimidazolylporphyrin, MnTDE-2-ImP$^{5+}$ is 118 mV more positive than of ortho ethylpyridylporphyrin, MnTE-2-PyP$^{5+}$ (+228 mV vs NHE), as a consequence of charge delocalization. A similar difference of 114 mV was seen between their methoxyethyl analogues. Mn porphyrins bearing N-pyridyl substituents of the same length, MnTnBu-PyP$^{5+}$ and MnTMOE-2-PyP$^{5+}$, have nearly identical $E_{1/2}$ of +254 and +251 mV vs NHE, which is 26 and 23 mV higher than that of MnTE-PyP$^{5+}$.

Electrospray mass spectrometry. ESMS has proven invaluable in identifying metal-free porphyrins and their Mn complexes (Batinic-Haberle et al, J. Chem. Soc., Dalton Trans., pgs. 2689-2696 (2002), Batinic-Haberle et al, J. Porphyrins Phthalocyanines 4:217-227 (2000)). When done at low cone voltage of 20 V, the spectra clearly reflect solvation and ion pairing, redox properties, protonation/deprotonation pattern, and dealkylation of these compounds.

Figure 2:
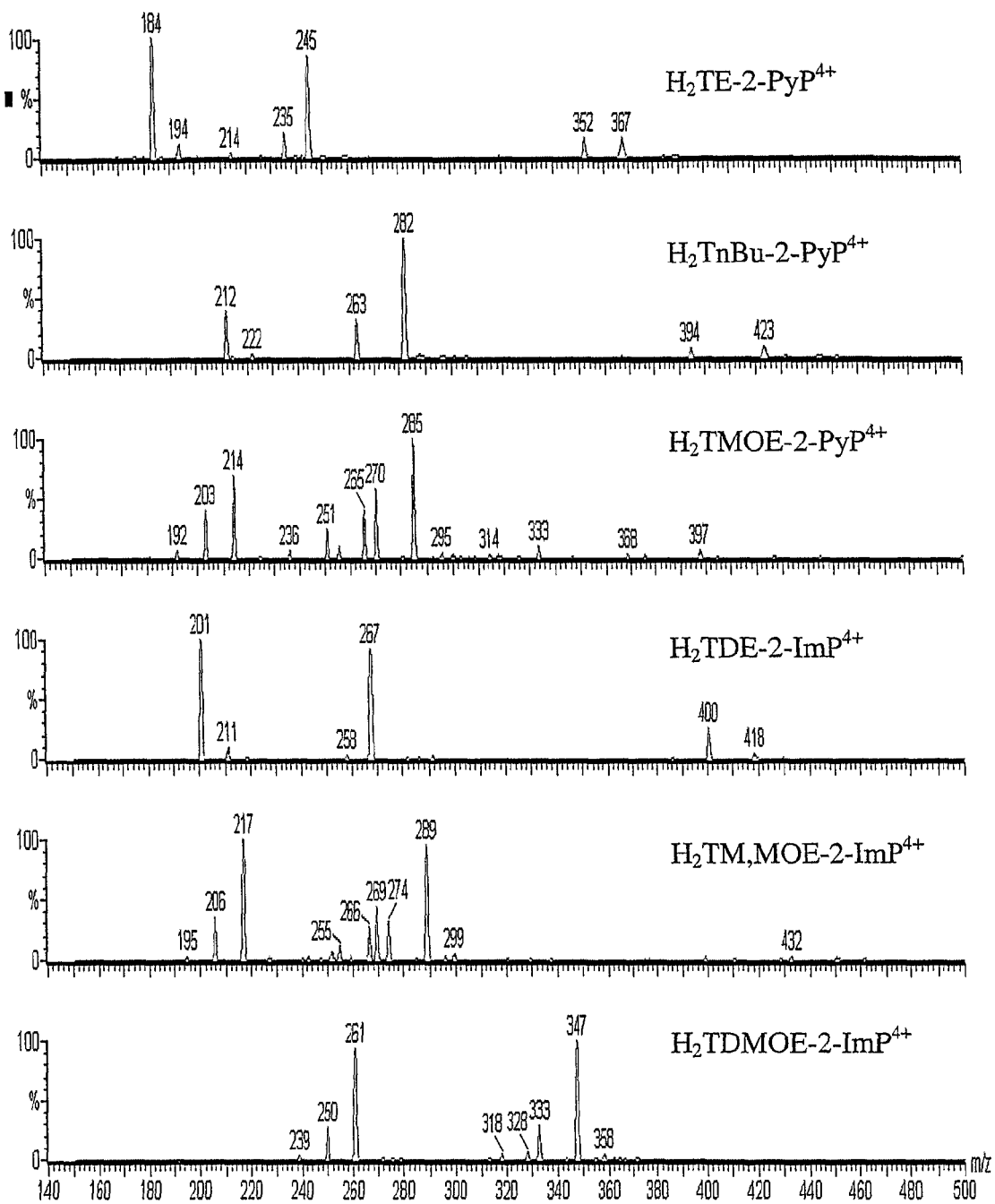
FIG. 2. ESMS of metal-free porphyrins obtained in water: acetonitrile=1:1 at 20 V cone voltage.

Metal-free porphyrins. ESMS at 20 V cone voltage. The ESMS spectra are shown in FIG. 2 and the assignments of peaks in Table 3. The ESMS of metal-free porphyrins showed dominant ions assigned to H$_2$P$^{4+}$/4 and/or its monodeprotonated analogue, H$_2$P$^{4+}$—H$^+$/3. As is the case with H$_2$TnBu-2-PyP$^{4+}$, the major peak in ESMS of its methoxyethyl analogue, H$_2$TMOE-2-PyP$^{4+}$, is the monodeprotonated species. Nearly equal abundances of molecular and monodeprotonated ions were observed with H$_2$TM,MOE-2-ImP$^{4+}$ and H$_2$TDMOE-2-ImP$^{4+}$. Negligible double deprotonation was observed in the case of H$_2$TMOE-2-PyP$^{4+}$ and minor peaks were noted with H$_2$TM,MOE-2-ImP$^{4+}$ and H$_2$TDMOE-2-ImP$^{4+}$. Only minor solvation was observed with H$_2$TE-2-PyP$^{4+}$ and H$_2$TMOE-2-PyP$^{4+}$.

Methoxyethyl porphyrins are more prone to fragmentation when compared to their alkylated analogues. Loss of ethyl or methoxyethyl groups is less frequent with di-ortho substituted imidazolyl porphyrins. This may be due to the stabilization of these porphyrins by ethyl(methyl) or methoxyethyl chains distributed both above and below the porphyrin plane. The most stable towards fragmentation is H$_2$TDE-2-ImP$^{4+}$, which undergoes negligible loss of an ethyl group (2.5% abundance) in contrast to H$_2$TE-2-PyP$^{4+}$ where 25% of monodeethylated species was seen. No loss of methyl groups were observed in the ESMS of H$_2$TM,MOE-2-ImP$^{4+}$.

In addition to the loss of methoxyethyl groups, species consistent with the loss of .CH$_2$OCH$_3$ were observed. These can only result from the fission within N$^+$—CH$_2$—CH$_2$—O—CH$_3$. Similar findings were previously reported for mesoporphyrin-IX dimethyl ester, where the so-called "benzylic" fission of .CH$_2$—COO—CH$_3$ from methyl propionate was detected (Smith, Mass Spectrometry of Porphyrins and Metalloporphyrins in Porphyrins and Metalloporphyrins, Smith, ed., Elsevier Scientific Publishing Company, Amsterdam, p. 388 (1975)).

ESMS at 30 V cone voltage. At higher cone voltage the ratio of monodeprotonated to molecular ion increases. Also higher abundances of species that result from the loss of multiple N-pyridyl substituents were seen. Again, the most stable compound was H$_2$TDE-2-ImP$^{4+}$ where no loss of two ethyl groups was observed. With H$_2$TDMOE-2-ImP$^{4+}$ only negligible loss of two methoxyethyl groups were observed.

Figure 3:
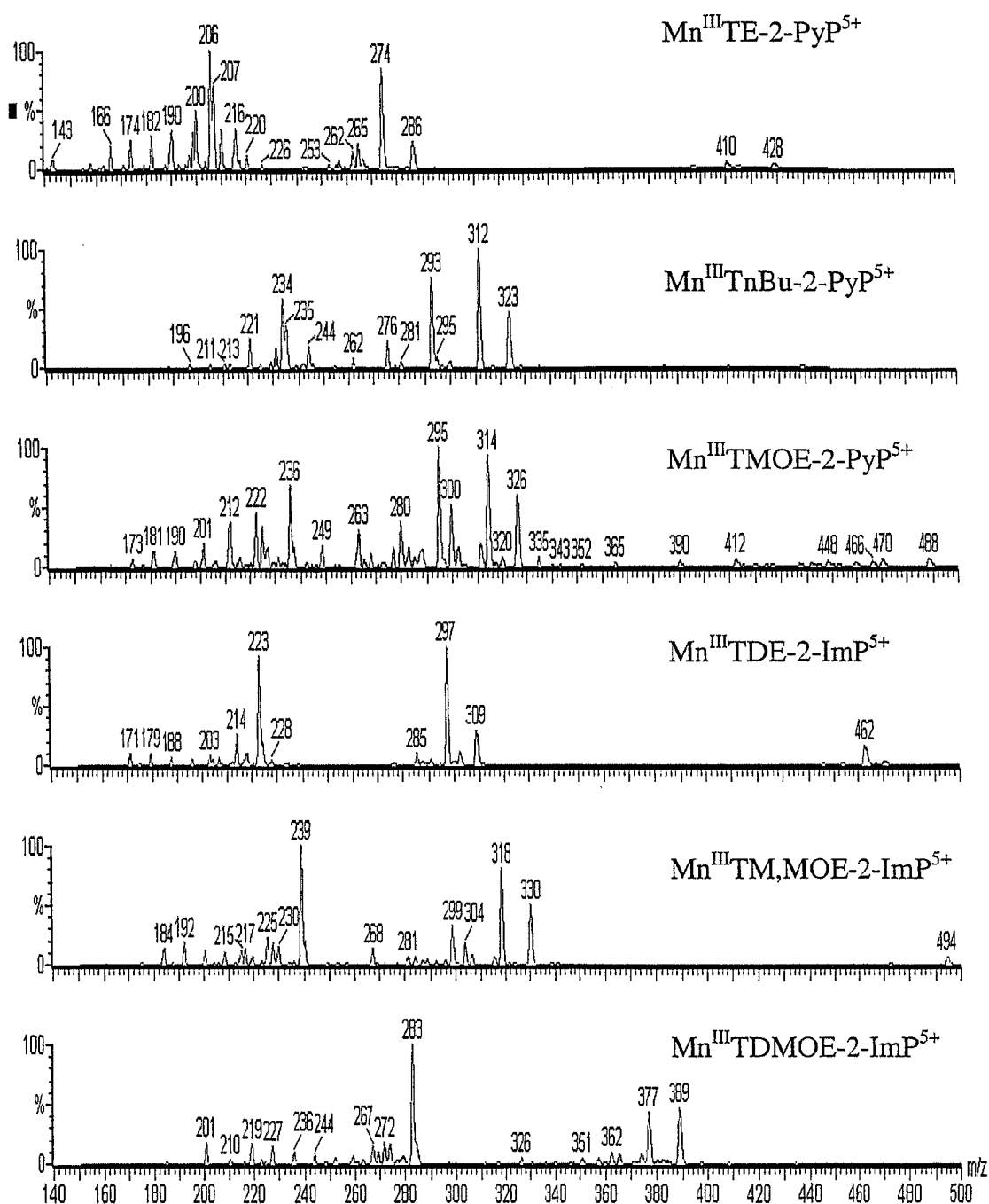
FIG. 3. ESMS of Mn(III) porphyrins obtained in water: acetonitrile=1:1 at 20 V cone voltage.

Mn(III) porphyrins. ESMS at 20 V cone voltage. The ESMS spectra are shown in FIG. 3, and the assignments of peaks are given in Table 3. Species solvated with 1 to 5 acetonitriles were observed. The negligible solvation of parent ligands argues for the location of solvent molecules around the metal site. The least solvated is the most lipophilic MnTnBu-2-PyP$^{5+}$.

Molecular ions were detected at low abundance. All Mn porphyrins studied undergo facile reduction. Thus, in ESMS spectra, the major peaks that are of similar intensities, relate to the oxidized and reduced Mn porphyrins associated with one or two chlorines. The longer the N-pyridyl and N,N'-diimidazolyl substituents the higher abundance of species associated with two chlorines. In addition, due to hydrogen bonding, higher abundances of chlorinated ions were seen in the ESMS of methoxyethyl compounds when compared to their alkyl analogues. The abundances of oxidized and reduced species were nearly identical in each of the ESMS other than in the case of MnTDMOE-2-ImP$^{5+}$, where more of the oxidized species was seen. This observation is surprising in view of its high $E_{1/2}$, but is consistent with it showing the lowest $k_{cat}$ among the methoxyethyl compounds. In the spectra of all methoxyethyl compounds doubly reduced species were seen. Similar observations with n-butyl, n-hexyl and n-octyl porphyrins were previously reported, and such peaks were assigned to species that are doubly reduced at the metal site ($Mn^{I}P^{3+}/3$) or at both the metal site and porphyrin ring ($Mn^{II}P^{3+}\cdot/3$).

Mn(III) pyridyl porphyrins that bear n-butyl or methoxyethyl groups of the same overall chain length have very similar patterns of fragmentation. In their ESMS major peaks that are of similar abundances, relate to the monochlorinated reduced porphyrin and monochlorinated species that lost one N-pyridyl substituent. $MnTMOE-2-PyP^{5+}$ is more hydrophilic, permitting increased hydrogen bonding inside the cavity. Therefore, more solvated species, species that lost charged N-pyridyl substituent/s and the species associated with two chlorines were observed.

As was the case with the metal-free ligands, Mn methoxyethyl porphyrins are more prone to fragmentation than their alkyl analogues. As with the ligands, Mn di-ortho imidazolyl porphyrins become stabilized towards fragmentation. Namely, only minor loss of methoxyethyl ($MnTDMOE-2-ImP^{5+}$) or ethyl ($MnTDE-2-ImP^{5+}$) groups was seen. The same has been previously observed with long-chain N-alkylpyridylporphyrins such as the n-hexyl and n-octyl compounds (Batinic-Haberle et al, J. Chem. Soc., Dalton Trans., pgs. 2689-2696 (2002)). Thus, the abundance of monodealkylated species was increased from methyl to n-butyl, and decreased from n-butyl to n-octyl (Batinic-Haberle et al, J. Chem. Soc., Dalton Trans., pgs. 2689-2696 (2002)). As with the ligands, fission within $N^+$—$CH_2$—$CH_2$—$O$—$CH_3$ was observed with loss of the .$CH_2$—$O$—$CH_3$ radical (Smith, Mass Spectrometry of Porphyrins and Metalloporphyrins in Porphyrins and Metalloporphyrins, Smith, ed., Elsevier Scientific Publishing Company, Amsterdam, p. 388 (1975)).

ESMS at 30 V cone voltage. At the higher cone voltage, solvation was only observed with $MnTDMOE-2-ImP^{5+}$ suggesting that it has a large capacity for hydrogen bonding due to the highest overall number of oxygen atoms. At higher cone voltage the abundance of oxidized species is greatly decreased. The major ions correspond to the monochlorinated reduced species except in the case of $MnTDMOE-2-ImP^{5+}$, where the abundance of reduced species has been increased by a mere 5% when compared to the ESMS obtained at 20 V. More of the monodealkylated and monodemethoxylated species were observed at higher cone voltage except in the ESMS of $MnTDMOE-2-ImP^{5+}$. No significant differences in fragmentation at 20 V and 30 V were observed for MnTDMOE-2-Imp$^{5+}$.

Catalysis of $O_2^-$ dismutation. Pulse radiolysis was used to assess the SOD-like activities of the Mn porphyrins studied. The initial concentration of $O_2^-$ produced by the pulse was about 27 µM, and the concentration of the Mn porphyrin was between 0.5 and 5 µM. The dismutation of $O_2^-$ was followed at 280 nm. The catalytic rate constant was determined from the linear dependence of $k_{obs}$ upon the concentration of the catalyst (Batinic-Haberle et al, Inorg. Chem. 40:726 (2001)). The log $k_{cat}$ values are summarized in Table 1. All the new compounds have high $O_2^-$ dismuting ability. The magnitude of the catalysis is due to the interplay of the electron-withdrawing effects of quaternized ortho pyridyl or di-ortho imidazolyl groups, favorable electrostatics, and the solvation of the metal site.

With N-alkylpyridylporphyrins, it was previously observed that lipophilicity, i.e. desolvation of the porphyrinic compounds, led to increased $E_{1/2}$. This is because the more deshielded positive N-pyridyl charges impose a stronger electron-withdrawing effect. Therefore, $MnTnBu-2-PyP^{5+}$ has higher $E_{1/2}$ value than $MnTE-2-PyP^{5+}$, but is catalytically less potent (Table 1). Such data had been previously explained by the interplay of solvation and electrostatic/steric effects (Batinic-Haberle et al, J. Chem. Soc., Dalton Trans., pgs. 2689-2696 (2002)). In this study, evidence arose in support of a dominant solvation effect and is discussed below. Namely, methoxyethylpyridylporphyrin was synthesized that has N-pyridyl substituents of the same size that impose similar steric effects as do n-butyl side chains in $MnTnBu-2-PyP^{5+}$. In addition, $MnTMOE-2-PyP^{5+}$ and $MnTnBu-2-PyP^{5+}$ have the same $E_{1/2}$, but $MnTMOE-2-PyP^{5+}$ has 6-fold higher $k_{cat}$ (Table 1). The methoxyethyl compound is more hydrated mostly due to the promotion of hydrogen bonding induced by the presence of oxygen in place of the —$CH_2$ group in contrast to the lipophilic n-butyl porphyrin. Therefore, the differences in local dielectric constant alone may be responsible for the higher $k_{cat}$ value obtained in the case of $MnTMOE-2-PyP^{5+}$. Such an observation agrees well with the explanation offered by Ferrer-Sueta et al for the reaction of Mn(III) N-alkylpyridylporphyrins with $ONOO^-$ (Ferrer-Sueta et al, J. Biol. Chem. 278:27432-27438 (2003)). Those authors observed equal sensitivity of $pK_{a,ax}$ (acid dissociation constant of the axially bound water), and $k(ONOO^-)$ to the changes in the length of the alkyl chains, as reported here with $k_{cat}$. Since the proton dissociation of an axial water is a unimolecular process, such observations can only be ascribed to changes in the local dielectric constant (Batinic-Haberle et al, J. Chem. Soc., Dalton Trans., pgs. 2689-2696 (2002)). That presumably accounts also for the observed sensitivity of metallation and demetallation rates of Mn(III) N-alkylpyridylporphyrins to the changes in the length of alkyl chains (Espenson, Chemical Kinetics and Reaction Mechanisms, McGraw-Hill Book Company, New York, p. 172 (1981)).

Kinetic salt effect. The effect of the ionic strength (µ) on the catalytic rate constant was assessed using eq [1] which is based on Debye-Huckel relation (Hambright et al, J. Porphyrins Phthalocyanines 7:139-146 (2003)) for the effect of the ionic strength of the solution on the activity coefficient of an ion.

$$\log k = \log k_{ref} + 2\,Az_A z_B \mu^{1/2}/(1+\mu^{1/2}) \qquad [1]$$

The k is the rate constant at any given ionic strength, while $k_{ref}$ is the rate constant at µ=0. The A is a collection of physical constants with a value of 0.509 and $z_A$ and $z_B$ are the charges of the reacting species. The equation predicts a linear plot of log k vs $\mu^{1/2}/(1+\mu^{1/2})$. Eq [1] assumes a coefficient of 1.0 ($\beta a_i$) for $\mu^{1/2}$ in the denominator, i.e., the distance of the closest approach, $a_i$ to be 3 Å and β is a physical constant, $0.33 \times 10^{-10} m^{-1}$. It is doubtful whether great significance can be attributed to the $a_i$, thus to the product $z_A z_B$ (Hambright et al, J. Porphyrins Phthalocyanines 7:139-146 (2003)), especially so in the light of the bulkiness, high charge and solvation shell of the metalloporphyrins. Accounting for the mono- and diprotonated phosphates as the major species at pH 7.8 ($pK_a$=7.2), and the concentration of the NaCl, the ionic strength was calculated using equation $\mu=\frac{1}{2}\Sigma m_i z_i^2$ where $m_i$ is the molality and $z_i$ the charge of the given ion.

Figure 4:
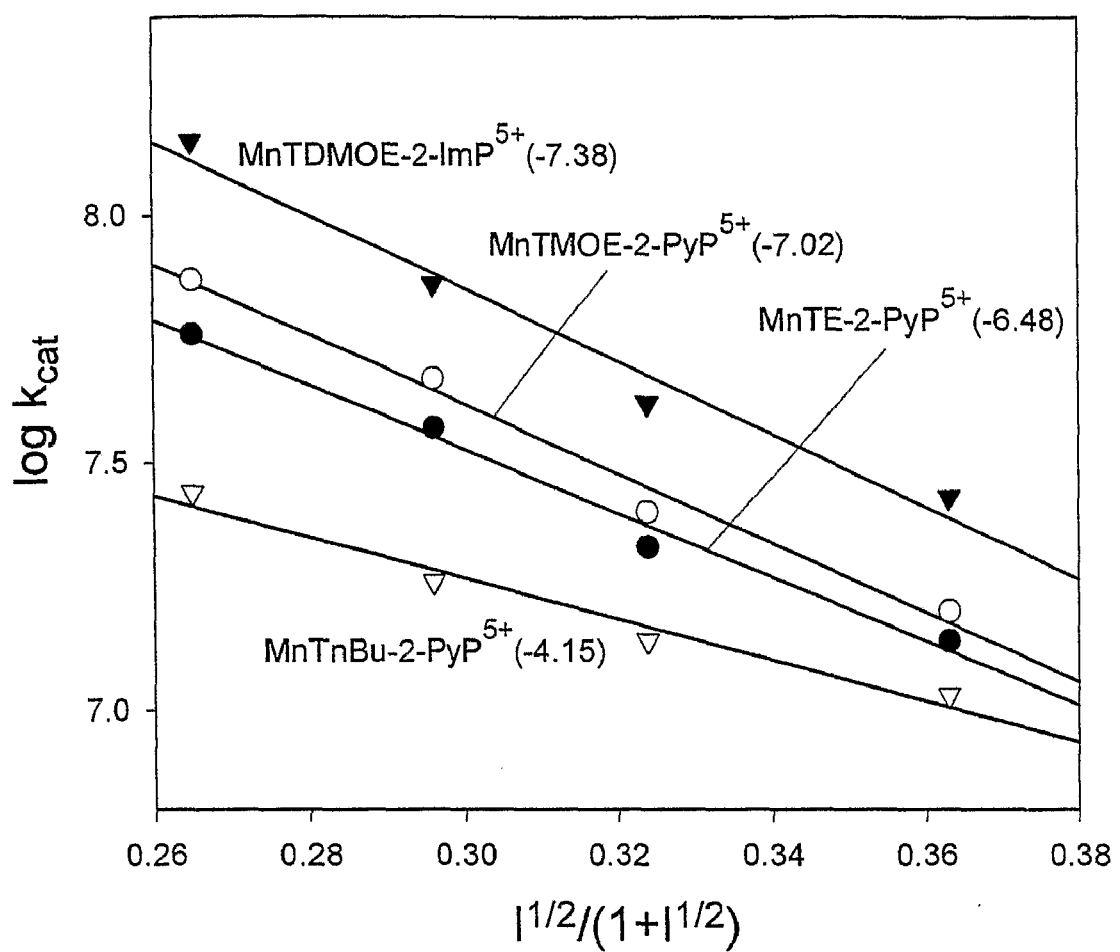
FIG. 4. Log $k_{cat}$ vs $\mu^{1/2}/(1+\mu^{1/2})$ for $Mn^{III}TE-2-PyP^{5+}$, $Mn^{III}TnBu-2-PyP^{5+}$, $MnTMOE-2-PyP^{5+}$ and $Mn^{III}TD-MOE-2-ImP^{5+}$ obtained in 0.05 M phosphate buffer, pH 7.8, 0-0.4 M NaCl. Slopes are given in parentheses.

Linear plots of log $k_{cat}$ vs $\mu^{1/2}/(1+\mu^{1/2})$ (eq [1]) are presented in FIG. 4. The slopes of the plots are −6.48 ($MnTE-2-PyP^{5+}$), −7.02 ($MnTMOE-2-PyP^{5+}$), −7.38 ($MnTDMOE-2-ImP^{5+}$), and −4.15 ($MnTnBu-2-PyP^{5+}$). As expected (Hambright et al, J. Porphyrins Phthalocyanines 7:139-146 (2003)), when the reactants are ions of opposite charges, the higher the ionic strength of the solution the lower the rate constants, i.e. the slopes are negative. The slopes of the plots indicate clearly the impact of the local dielectric constant on the $k_{cat}$. The $k_{cat}$ of the most lipophilic compound, MnTnBu-2-PyP$^{5+}$ is 40% less sensitive to the changes in ionic strength of the solution than is the $k_{cat}$ of its methoxyethyl analogue, MnTMOE-2-PyP$^{5+}$.

Aerobic growth of *E. coli*. The effects of the Mn porphyrin mimics of SOD activity on the aerobic growth of SOD-deficient and wild type *E. coli* were examined in both the 5AA minimal and M9CA media, under aerobic conditions.

5AA minimal medium. FIGS. 5A and 5B show that the growth of the wild type *E. coli* in 5AA minimal medium was not significantly influenced by these compounds up to 25 μM with the exception of the n-hexyl and n-octyl porphyrins which were toxic, Thus at 3 μM n-hexyl slowed the growth (line 6, FIG. 5A) while the n-octyl porphyrin completely inhibited growth of the wild type *E. coli* (line, FIG. 5A). In contrast, the SOD-deficient strain could not grow in the 5AA minimal medium (lines 1 in 5C and 5D), and the SOD mimics facilitated growth. Thus the n-hexyl porphyrin was most effective at 3 μM (line 6 in FIG. 5C), and the n-butyl analogue was nearly as effective (line 5 in FIG. 5C). The MnTDMOE-2-PyP$^{5+}$ (line 11 in FIG. 5C) was the most effective methoxyethyl porphyrin, and was more protective than MnTE-2-PyP$^{5+}$ (line 3, FIG. 5C) and MnTDE-2-ImP$^{5+}$ (line 9, FIG. 5C). When tested at 25 μM the MnTE-2-PyP$^{5+}$ and its n-propyl analogue were most effective (lines 3 and 4, FIG. 5D); with methyl, methoxyethylpyridyl and dimethoxyethylimidazolyl porphyrins not far behind (FIG. 5D, lines 2, 5, 8 and 11). The n-hexyl porphyrin that had complemented at 3 μM (line 6 in FIG. 5C) failed to do so at 25 μM; presumably due to toxicity at the higher concentration. The insets in FIGS. 5C and 5D allow more rapid assessment of the effects of these compounds on the growth of the SOD-deficient *E. coli*.

M9CA medium. Similar to the case in 5AA minimal medium, all of the porphyrins, other than longer alkyl chain analogues, were not toxic to wild type *E. coli*, up to 30 μM levels. Thus, at 30 μM n-hexyl and n-octyl compounds prevented wild type *E. coli* to grow, while only marginal toxicity was observed with 30 μM n-butyl. Although unable to grow in aerobic minimal medium, the SOD-deficient strain does grow slowly in M9CA medium. The effects of 1, 3, 10 and 30 μM SOD mimics on the growth of the SOD-deficient strain are presented in FIGS. 6A-D. The n-hexyl porphyrin was most effective at 1 and 3 μM (line 6 in FIGS. 6A and 6B), but was progressively less effective at 10 and 30 μM (line 6 in FIGS. 6C and 6D); undoubtedly due to its toxicity at these high concentrations. The n-butyl analogue, that was most effective at 10 and 30 μM, was less effective in promoting growth at 1 and 3 μM (line 5 in FIGS. 6A-D).

MnTM-2-PyP$^{5+}$, MnTME-2-PyP$^{5+}$, MnTnPr-2-PyP$^{5+}$, MnTDE-2-ImP$^{5+}$, as well as methoxyethyl porphyrins facilitated aerobic growth of SOD-deficient *E. coli* in concentration-dependent manner. At 1 μM all of them (lines 2, 3, 4, 8-11, FIG. 6B) offered low protection to SOD-deficient *E. coli*. At 3 μM levels MnTDMOE-2-ImP$^{5+}$ (line 11 in FIG. 6B) was the most effective (next to n-butyl and n-hexyl), and was more protective than MnTE-2-PyP$^{5+}$ (line 3, FIG. 6B), while MnTDE-2-ImP$^{5+}$ was ineffective (line 9, FIG. 6B). At 30 μM all of them offered either much higher or near full protection to SOD-deficient *E. coli* (lines, 2-4, 8-11, FIG. 6D).

Figure 5:
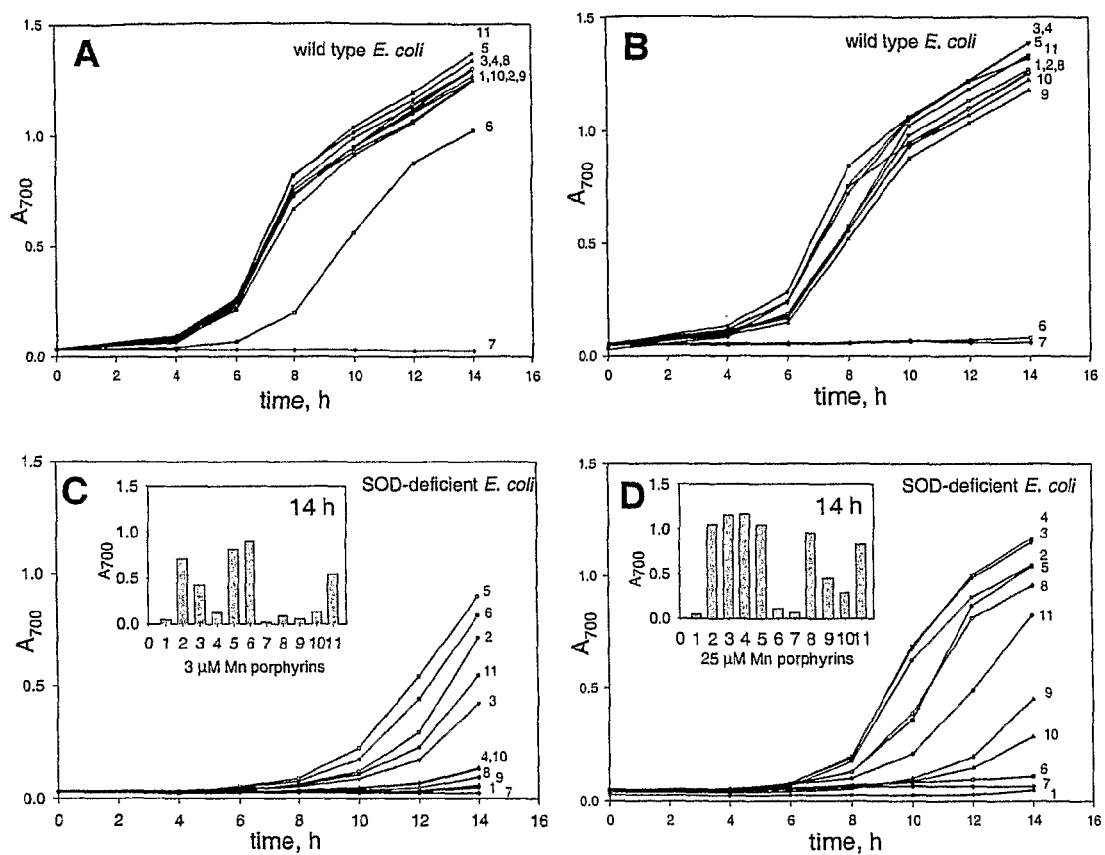
FIGS. 5A-5D. Aerobic growth curves of wild type (FIGS. 5A, 5B) and SOD-deficient *E. coli* (FIGS. 5C, 5D) in minimal 5AA minimal medium in the absence (1) and presence of 3 μM (FIGS. 5A, 5C), and 25 μM Mn(III) porphyrins (FIGS. 5B, 5D). Mn porphyrins are abbreviated as follows: MnT(alkyl)-2-PyP$^{5+}$, alkyl being methyl (2), ethyl (3), n-propyl (4), n-butyl (5), n-hexyl (6), n-octyl (7), MnTMOE-2-PyP$^{5+}$ (8), MnTDE-2-ImP$^{5+}$ (9), MnTM,MOE-2-PyP$^{5+}$ (10), MnTDMOE-2-ImP$^{5+}$ (11). Inset: Aerobic growth of SOD-deficient *E. coli* in 5AA minimal medium ($A_{700\ nm}$) after 14 hours in the presence of 3 μM (FIG. 5C) and 25 μM (FIG. 5D) Mn porphyrins.
Figure 6:
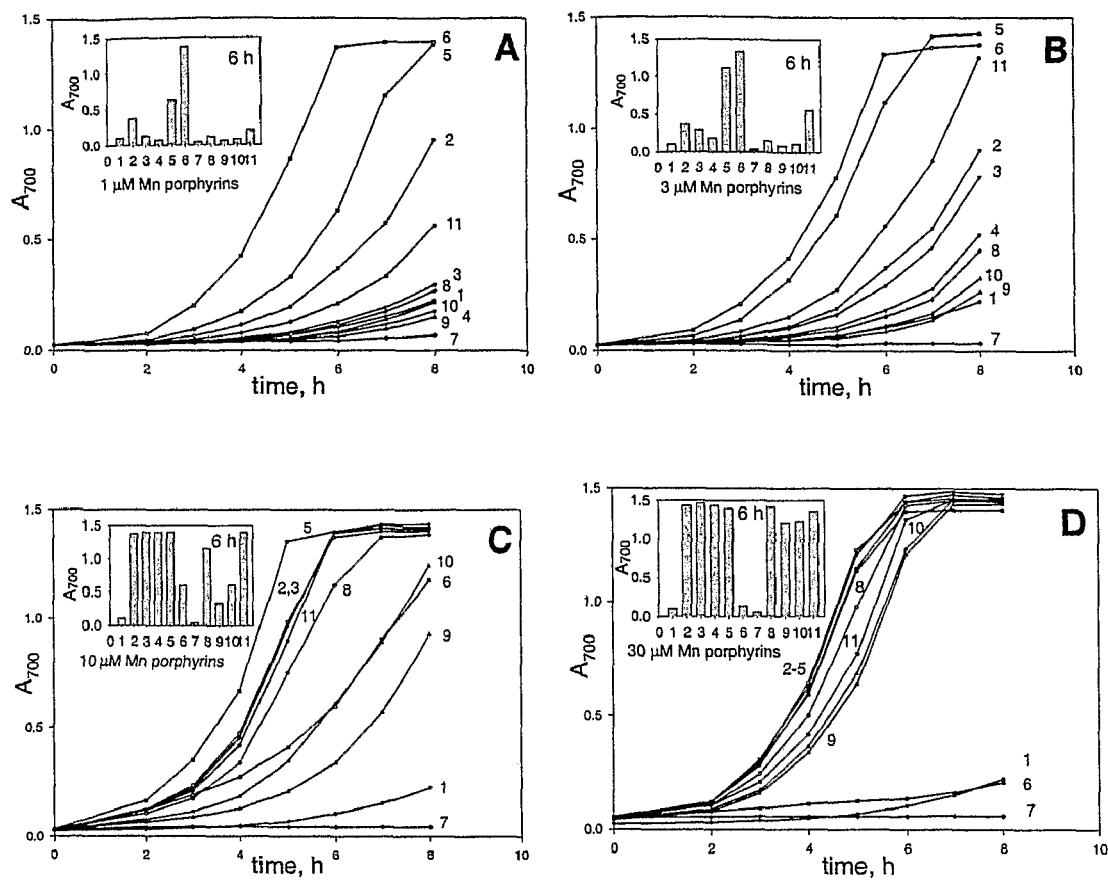
FIGS. 6A-6D. Aerobic growth curves of SOD-deficient *E. coli* in M9CA medium in the absence (1) and presence of 1 μM (FIG. 6A), 3 μM (FIG. 6B). 10 μM (FIG. 6C) and 30 μM (FIG. 6D) Mn porphyrins. Mn porphyrins are abbreviated as in FIG. 5. Inset: Aerobic growth of SOD-deficient *E. coli* in M9CA medium after 6 hours ($A_{700\ nm}$) in the absence (1) and presence of 1 μM (FIG. 6A), 3 μM (FIG. 6B), 10 μM (FIG. 6C) and 30 μM (FIG. 6D) Mn porphyrins.
Figure 7:
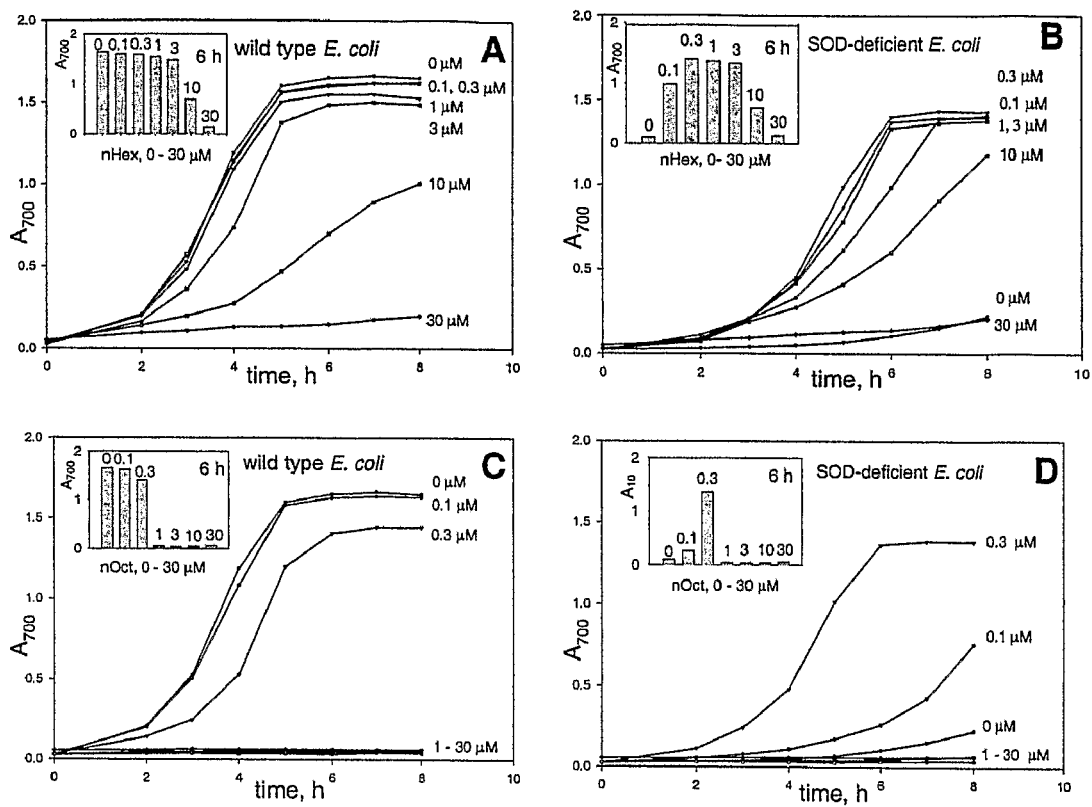
FIGS. 7A-7D. Aerobic growth curves of wild type (FIGS. 7A, 7C) and SOD-deficient *E. coli* (FIGS. 7B, 7D) in M9CA medium in the presence of 0, 0.1, 0.3, 1, 3, 10 and 30 μM MnTnHex-2-PyP$^{5+}$ (nHex) (FIGS. 7A, 7B) and MnTnOct-2-PyP$^{5+}$ (nOct) (FIGS. 7C, 7D). Inset: Aerobic growth of *E. coli* in M9CA medium after 6 hours ($A_{700\ nm}$ in the presence of 0, 0.1, 0.3, 1, 3, 10 and 30 μM MnTnHex-2-PyP$^{5+}$ (nHex) (FIGS. 7A, 7B) and MnTnOct-2-PyP$^{5+}$ (nOct) (FIGS. 7C, 7D).

The data in FIGS. 5 and 6 show that the long chain alkyl groups provide great efficacy that was offset by a concentration-dependent toxicity. It was therefore of interest to examine the growth promoting activity of the n-hexyl and n-octyl porphyrins over a wide range of concentrations. The effects of these compounds in the range of 0.1 to 30 μM on the growth of both SOD-deficient and SOD-proficient strains are presented in FIGS. 7A-D. FIG. 7A shows that the n-hexyl begins to exert toxicity on the parental strain at 3 μM. FIG. 7C demonstrates the greater toxicity of the octyl compound that becomes observable already at 0.3 μM. The n-butyl compound exerted marginal toxicity at 30 μM. Therefore, it appears that for each increase in the number of carbon atoms by 2 ($CH_2$—$CH_2$—) from n-butyl to n-octyl, the toxicity increases ~10-fold.

In accord with these results, the n-hexyl compound was most able to facilitate the growth of SOD-deficient strain between 0.3 and 3 μM (FIG. 7B), while the utility of n-octyl porphyrin was restricted to $\leq$0.3 μM (FIG. 7D). At 0.3 μM n-hexyl and n-octyl porphyrins (FIGS. 7B and 7D) are equally protective as are 10 μM MnTM-2-PyP$^{5+}$, MnTE-2-PyP$^{5+}$ and MnTDMOE-2-ImP$^{5+}$ (FIG. 6C, lines 2, 3 and 11).

Catalysis of $O_2.^-$ dismutation in the presence and absence of *E. coli* cell extract. It has been previously found that ortho MnTM-2-PyP$^{5+}$ associates less with DNA and RNA as compared to the planar para isomer, MnTM-4-PyP$^{5+}$ (Batinic-Haberle et al, J. Biol. Chem. 273:24521-24528 (1998)). Consequently, MnTM-4-PyP$^{5+}$ was able to catalyze $O_2.^-$ dismutation in the presence of *E. coli* cell extract only if nucleic acids were removed from it. Further, Tjahjono et al (Tjahjono et al, Biochim. Biophys. Acta 1472:333-343 (1999)) reported that diortho metal-free tetrakis(N,N'-dimethylimidazolium-2-yl)porphyrin interacted with calf thymus DNA ~10-fold less than $H_2$TM-4-PyP$^{4+}$. In line with these findings, all of the new compounds would not associate with nucleic acids as they are non-planar, bulky, either ortho pyridyl- or diorthoimidazolyl-substituted porphyrins. Thus, they exhibited the same SOD-like activity in the presence and absence of *E. coli* cell extract.

Discussion $O_2.^-$ dismuting ability of Mn porphyrins. A linear relationship has been established between the log $k_{cat}$ for the $O_2.^-$ dismutation (eqs [2] and [3])$^3$ and metal-centered redox potential of Mn(III)

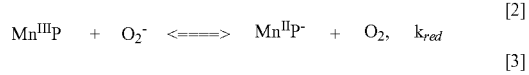
[2]

Figure 8:
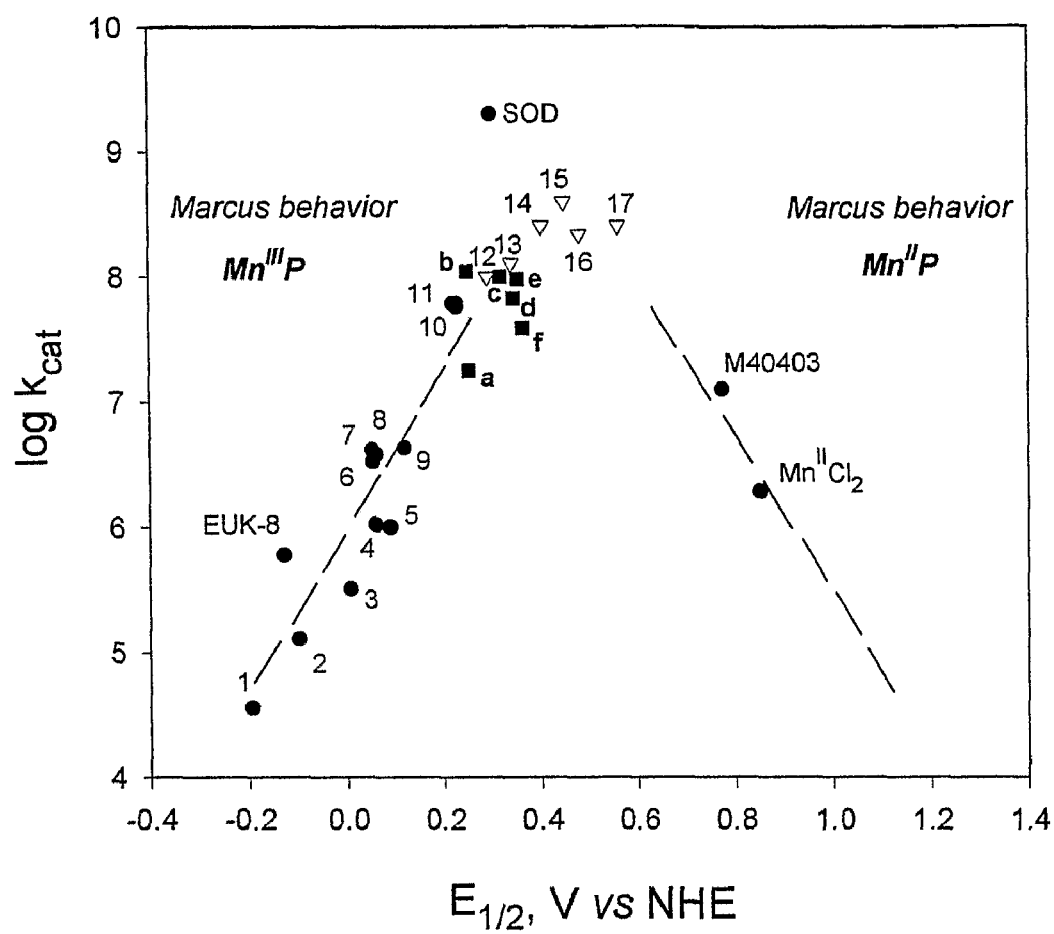
FIG. 8. Reactivity of manganese complexes expressed in terms of log $k_{cat}$ vs metal-centered redox potential, $E_{1/2}$. Only water-soluble Mn(III) porphyrins are given in the left, linear section of the curve that obeys Marcus equation (Marcus, Annu. Rev. Phys. Chem. 15:155 (1964), Jordan, Reaction Mechanisms of Inorganic and Organometallic Systems, 2$^{nd}$ Ed., Oxford University Press, New York, (1998), Bennet, Prog. Inorg. Chem. 18:1-176 (1973)) and data are from Batinic-Haberle et al, Inorg. Chem. 38:4011-4022 (1999): (1) MnTCPP$^{3-}$, (2) MnT(TMAP)$^{5+}$, (3) MnT(2,6-F$_2$-3-SO$_3$—P)P$^{3-}$, (4) MnT(TFTMAP)P$^{5+}$, (5) MnT(2,6-Cl$_2$-3-SO$_3$—P)P$^{3-}$, (6) MnBM-2-PyP$^{3+}$, (7) MnTM-3-PyP$^{3+}$, (8) MnTM-4-PyP$^{3+}$, (9) MnTr-2-PyP$^{4+}$, (10) MnTM-2-PyP$^{5+}$, (11) MnTE-2-PyP$^{5+}$. Data for EUK-8 and MnCl$_2$ are from Batinic-Haberle et al, Inorg. Chem. 40:726 (2001), data for Mn(II) cyclic polyamine M40403 from Aston et al, Inorg. Chem. 40:1779 (2001). Data for SOD are from (Ellerby et al, J. Am. Chem. Soc. 118:6556 (1996), Vance and Miller, J. Am. Chem. Soc. 120:461 (1998), Klug-Roth et al, J. Am. Chem. Soc. 95:2786 (1973). Data for Mn$^{III}$Cl$_{1-4}$MnTE-4-PyP$^{5+}$ (12-15) are from Kachadourian et al, Inorg. Chem. 38:391-396 (1999), data for Mn$^{II}$Br$_8$MnTM-4-PyP$^{4+}$ (16) are from Batinic-Haberle et al, Arch. Biochem. Biophys. 343:225 (1997), and for Mn$^{II}$Cl$_5$MnTE-2-PyP$^{4+}$ (17) from Kachadourian et al, Free Radic. Biol. Med. 25 (Suppl. 1):S17 (1998) (triangles). Data for MnTnBu-2-PyP$^{5+}$ (a) are from Batinic-Haberle et al, J. Chem. Soc., Dalton Trans., pgs. 2689-2696 (2002), and for MnTMOE-2-PyP$^{5+}$ (b), MnTD(M)E-2-ImP$^{5+}$ (c,d), MnTM,MOE-2-PyP$^{5+}$ (e), and MnTDMOE-2-ImP$^{5+}$ (f) are from the present work (squares).

[3]

porphyrins (Batinic-Haberle et al, Inorg. Chem. 38:4011-4022 (1999)). The relationship obeys the Marcus equation (Marcus, Annu. Rev. Phys. Chem. 15:155 (1964), Jordan, Reaction Mechanisms of Inorganic and Organometallic Systems, 2$^{nd}$ Ed., Oxford University Press, New York (1998), Bennet, Prog. Inorg. Chem. 18:1-176 (1973)) whereby $k_{cat}$ increases 10-fold with each 120 mV increase in $E_{1/2}$. The Marcus equation, for outer-sphere one-electron transfer reactions (Marcus, Annu. Rev. Phys. Chem. 15:155 (1964)) is applicable because $k_{cat}$ is determined by the rate-limiting reduction of Mn(III) porphyrins with $O_2.^-$ (eq [2], see the rising limb of the bell shape curve in FIG. 8). The most potent catalysts which emerge from this structure-activity relationship, MnTM-2-PyP$^{5+}$ and MnTE-2-PyP$^{5+}$, owe their potency to the electron-withdrawing effect of quaternized ortho pyridyl nitrogens. These ortho porphyrins are more bulky than their planar para isomers, and that minimizes the unfavorable interactions with DNA and RNA; a vital property if the compounds are to be used as SOD mimics in vivo. At +228 mV vs NHE (1,2,5) the reduction of MnTE-2-PyP$^{5+}$ by $O_2.^-$ proceeds with a rate constant of $2.5\times10^7$ M$^{-1}$ s$^{-1}$ and oxidation by $8.2\times10^7$ M$^{-1}$ s$^{-1}$ (1). That is the case because the midway potential (+360 mV vs NHE) for the reduction and oxidation of $O_2.^-$ is being approached, which provides an equal thermodynamic driving force for both half-reactions of catalytic cycle (eqs [2] and [3]). Thus, Cu,Zn-SOD with $E_{1/2}$ of ~+300 mV vs NHE reduces and oxidizes $O_2.^-$ with equal rate constants of $2\times10^9$ M$^{-1}$ s$^{-1}$ (pH 7.8) (Vance and Miller, Biochemistry 40:13079 (2001), (a) Lawrence and Sawyer, Biochemistry 18:3045 (1979), (b) Barrette et al, Biochemistry 22:624 (1983), Ellerby et al, J. Am. Chem. Soc. 118:6556 (1996), Vance and Miller, J. Am. Chem. Soc. 120:461 (1998), Klug-Roth et al, J. Am. Chem. Soc. 95:2786 (1973)). Any further increase or decrease in $E_{1/2}$ stabilizes Mn+2 or +3 oxidation state so that either oxidation of Mn(II) compounds (M40403 (Cuzzocrea et al, Br. J. Pharmacol. 132:19-29 (2001), Aston et al, Inorg. Chem. 40:1779 (2001), Riley, Adv. Supramol. Chem. 6:217-244 (2000), (a) Riley et al, Inorg. Chem. 35:5213 (1996), (b), Riley and Weiss, J. Am. Chem. Soc. 116:387 (1994)) and Mn$^{II}$Cl$_2$ (Batinic-Haberle et al, Inorg. Chem. 40:726 (2001)) or reduction of Mn(III) compounds, respectively, become rate-limiting step accompanied by a decrease in log $k_{cat}$. The Marcus equation is again obeyed in the region where the oxidation of Mn(II) compounds is a rate-limiting step (falling limb of FIG. 8). While the SOD-like activity of Mn porphyrins (Batinic-Haberle et al, Inorg. Chem. 38:4011-4022 (1999), Kachadourian et al, Inorg. Chem. 38:391-396 (1999), Batinic-Haberle et al, J. Chem. Soc., Dalton Trans., pgs. 2689-2696 (2002), Batinic-Haberle et al, Arch. Biochem. Biophys. 343:225 (1997), Kachadourian et al, Free Radic. Biol. Med. 25(Suppl 1):S17 (1998)) has been maximized thermodynamically, kinetic enhancement remains possible.

Study of the structural basis for the antioxidant ability of MnTE-2-PyP$^{5+}$ led to the design of the imidazolyl analogue, MnTDE-2-ImP$^{5+}$. Both compounds have been proven beneficial in different models of oxidative stress injuries (Tao et al, Circulation 108:2805-2811 (2003), Sheng et al, J. Neurotrauma, In press (2003), Sheng et al, Drug News and Perspectives 15:654-665 (2002), Sheng et al, Free Radic. Biol. Med. 33:947-961 (2002), Vujaskovic et al, Free Radic. Biol. Med. 33:857-863 (2002), Piganelli et al, Diabetes 51:347-355 (2002), Trostchansky et al, Free Radic. Biol. Med. 35:1293-1300 (2003), Mackensen et al, J. Neurosci. 21:4582-4592 (2001), Aslan et al, Proc. Natl. Acad. Sci. USA 98:15215-15220 (2001), Sheng et al, Free Radic. Biol. Med. In preparation (2003), Bottino et al, Diabetes 51:2561-2567 (2002), Bowler et al, Free Radic. Biol. Med. 33:1141-1152 (2002)). The MnTDE-2-ImP$^{5+}$ has both ortho imidazolyl nitrogens substituted with alkyl chains. The positive charge is thus delocalized over both nitrogens, providing greater proximity to the meso porphyrin carbons, which imposes a stronger electron-withdrawing effect than does the positively charged ortho pyridyl nitrogens. Consequently, MnTDE-2-Imp$^{5+}$ and other imidazolyl compounds synthesized in this work have more than 100 mV higher $E_{1/2}$ than analogous pyridyl porphyrins (Table 1). However, for the reasons discussed above, no further increase in $k_{cat}$ has been gained.

It has been shown that both $k_{cat}(O_2.^-)$ (Batinic-Haberle et al, J. Biol. Chem. 273:24521-24528 (1998), Batinic-Haberle et al, Inorg. Chem. 38:4011-4022 (1999), Batinic-Haberle et al, J. Chem. Soc., Dalton Trans., pgs. 2689-2696 (2002)) and the rate constant for ONOO$^-$ (Ferrer-Sueta et al, J. Biol. Chem. 278:27432-27438 (2003), Ferrer-Sueta et al, Chem. Res. Toxicol. 12:442-449 (1999)) reduction by Mn porphyrins are proportional to the electron-deficiency of the porphyrin (measured as $E_{1/2}$ for Mn$^{III}$/Mn$^{II}$ redox couple), and are thus proportional to each other (Ferrer-Sueta et al, J. Biol. Chem. 278:27432-27438 (2003)). It can therefore be expected that these new compounds will be effective scavengers of ONOO$^-$ as well. (Although the reduction of ONOO$^-$ involves the O=Mn$^{IV}$/Mn$^{III}$ redox couple, the dependence of the rate constant for ONOO$^-$ reduction by Mn(III) porphyrins upon the $E_{1/2}$ of Mn$^{III}$/Mn$^{II}$ redox couple is observed because the rate-limiting step in reduction of ONOO$^-$ is its binding to the manganese (Ferrer-Sueta et al, J. Biol. Chem. 278:27432-27438 (2003)). Further, as their reducibility is increased along with increased $E_{1/2}$, they would be more readily reduced by cellular reductants, whereby the pro-oxidant action of Mn(III) or O=Mn(IV) porphyrins would be prevented (Batinic-Haberle et al, J. Chem. Soc., Dalton Trans., pgs. 2689-2696 (2002), Trostchansky et al, Free Radic. Biol. Med. 35:1293-1300 (2003), Ferrer-Sueta et al, Chem. Res. Toxicol. 12:442-449 (1999), Bloodsworth et al, Free Radic. Biol. Med. 28:1017-1029 (2000)). As already mentioned, Mn porphyrins have the ability to scavenge a wide range of ROS and RNS. That may make them advantageous over more selective antioxidants such as cyclic polyamines (Cuzzocrea et al, Br. J. Pharmacol. 132:19-29 (2001), Aston et al, Inorg. Chem. 40:1779 (2001), Riley, Adv. Supramol. Chem. 6:217-244 (2000), (a) Riley et al, Inorg. Chem. 35:5213 (1996), (b), Riley and Weiss, J. Am. Chem. Soc. 116:387 (1994)), that were reported to lack reactivity towards $H_2O_2$, ONOO$^-$, NO and HClO (Cuzzocrea et al, Br. J. Pharmacol. 132:19-29 (2001)).

Improving bioavailability of Mn porphyrins. Stroke (Sheng et al, Free Radic. Biol. Med. 33:947-961 (2002)) and spinal cord injury (Sheng et al, Free Radic. Biol. Med. In preparation (2003)) studies indicate that the toxicity and bioavailability of MnTE-2-PyP$^{5+}$ and MnTDE-2-ImP$^{5+}$ could be favorably modified. The imidazolyl compound exerts 16-fold lower neurotoxicity in a stroke model than does the pyridyl compound (Sheng et al, Drug News and Perspectives 15:654-665 (2002), Sheng et al, Free Radic. Biol. Med. 33:947-961 (2002), Mackensen et al, J. Neurosci. 21:4582-4592 (2001)). Since both compounds are of similar in vitro antioxidant potency, the lower neurotoxicity of MnTDE-2-ImP$^{5+}$ was ascribed to its higher metal-centered redox potential and/or bulkiness as it has ethyl groups distributed above and below the porphyrin plane. However, possibly for the same reasons, MnTDE-2-ImP$^{5+}$ lacks protectiveness in spinal cord injury as compared to MnTE-2-PyP$^{5+}$ when both compounds are given intravenously (Sheng et al, Free Radic. Biol. Med. In preparation (2003)). In addition, the excessive hydrophilic character of both compounds limits their transport across the blood brain and spinal cord barrier and thus diminishes their ability to protect (Sheng et al, Free Radic. Biol. Med. 33:947-961 (2002)).

The lipophilicity and bulkiness of the parent compound, MnTE-2-PyP$^{5+}$, has been increased by increasing the length of N-pyridyl alkyl chains up to n-octyl (Batinic-Haberle et al, J. Chem. Soc., Dalton Trans., pgs. 2689-2696 (2002)). With no loss of antioxidant capacity the lipophilicity was increased nearly 10-fold from methyl to n-octyl compound (Batinic-Haberle et al, J. Chem. Soc., Dalton Trans., pgs. 2689-2696 (2002)), Table 1 and FIG. 9A, inset). The E. coli study shows that the increase in the alkyl chain length increases the toxicity of these compounds, so that 30 µM n-hexyl and n-octyl porphyrins prevent wild type E. coli from growing. In a separate experiment both metal-free n-octyl and its Mn(III) complex proved equally toxic. Thus, it may be the surfactant character, rather than the redox property, of the porphyrin that causes the toxicity. However, at 100-fold lower concentration (0.3 µM), the toxicity of n-hexyl and n-octyl compounds was mostly eliminated, and at 0.3 µM both compounds offered the same level of protection as the methyl and ethyl porphyrins did at 10 µM, and the n-butyl did at 3 µM.

Figure 9:
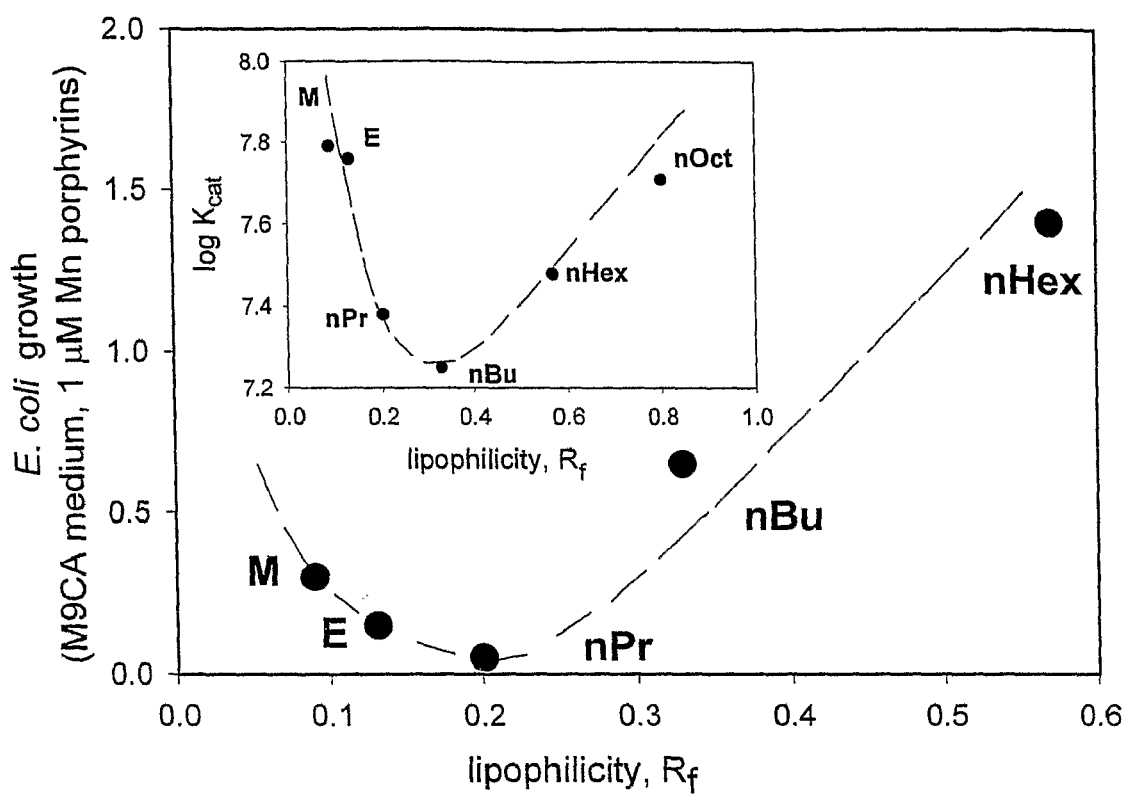
FIG. 9. Aerobic growth of SOD-deficient *E. coli* in M9CA medium after 6 hours, measured as $A_{700\ nm}$, in the presence of 1 μM Mn(III) N-alkylpyridylporphyrins as a function of their lipophilicity, $R_f$ (Table 1). Alkyl is methyl (M) ethyl (E), n-propyl (nPr), n-butyl (nBu), n-hexyl (nHex) and n-octyl (nOct). Inset: The log $k_{cat}$ of Mn(III) N-alkylpyridylporphyrins as a function of their lipophilicity, $R_f$.

FIG. 9 indicates a similarity by which in vitro SOD potency ($k_{cat}$) of N-alkylpyridylporphyrins and protection of SOD-deficient E. coli depend upon lipophilicity index, $R_f$. From methyl to n-propyl the protection of SOD-deficient E. coli decreases slightly as a consequence of the decrease in $k_{cat}$ (FIG. 6B, lines 2, 3 and 4). The decrease in $k_{cat}$ with increase in $R_f$ occurs because the ionic dismutation reactions are hindered by the local lipophilicity (FIG. 9A, inset). (From methyl to n-octyl metal-centered redox potential increases linearly with $R_f$ (Batinic-Haberle et al, J. Chem. Soc., Dalton Trans., pgs. 2689-2696 (2002)). As the lipophilicity increases further from n-butyl to n-octyl, the effect of the metal-centered redox potential prevails and $k_{cat}$ starts to increase (FIG. 9A, inset). Eventually, methyl and n-octyl are of same SOD-like potency (discussed in detail in Batinic-Haberle et al, J. Chem. Soc., Dalton Trans., pgs. 2689-2696 (2002)). The ability to protect E. coli follows the same trend; yet, rather than from n-butyl, it increases from n-propyl to n-octyl (lines 5 and 6 in FIG. 6B, FIG. 9). More importantly, the increase in protection increases at higher pace than does SOD-like activity. Therefore, a 30-fold higher protection of n-octyl vs methyl porphyrin is probably due to ~10-fold higher lipophilicity of n-octyl compound.

A new series of analogues of potent SOD mimics, MnTE-2-PyP$^{5+}$ and MnTDE-2-ImP$^{5+}$ have been described herein (FIG. 1). MnTMOE-2-PyP$^{5+}$ is a methoxyethyl analogue of MnTE-2-PyP$^{5+}$ with two-fold higher SOD-like activity. It is similarly bulky as MnTnBu-2-PyP$^{5+}$ since it has one —CH$_2$ group of each n-butyl chain replaced with oxygen. Moreover, such modification diminishes surfactant character of the alkyl chains. The MnTMOE-2-PyP$^{5+}$ has the same metal-centered redox potential of +251 mV vs NHE as the n-butyl compound (+254 mV vs NHE), but a 6-fold higher catalytic potency (Table 1), the highest among the Mn porphyrin-based SOD mimics thus far prepared. The enhanced antioxidant capacity when compared to the MnTnBu-2-PyP$^{5+}$ is due to the increased hydration of MnTMOE-2-PyP$^{5+}$ that favors ionic O$_2^-$ dismutation reactions (eqs [2] and [3]). Such a conclusion is also supported by a much greater sensitivity of the $k_{cat}$ of MnTMOE-2-PyP$^{5+}$ to the ionic strength variations (FIG. 4).

In the same manner, the imidazolyl compound, MnTDE-2-ImP$^{5+}$ has been modified. Two porphyrins were synthesized that have either all eight ethyl groups replaced by methoxyethyl chains (MnTDMOE-2-ImP$^{5+}$), or have the imidazole nitrogens substituted by four methyl and four methoxyethyl groups (MnTM,MOE-2-ImP$^{5+}$) (FIG. 1).

Figure 10:
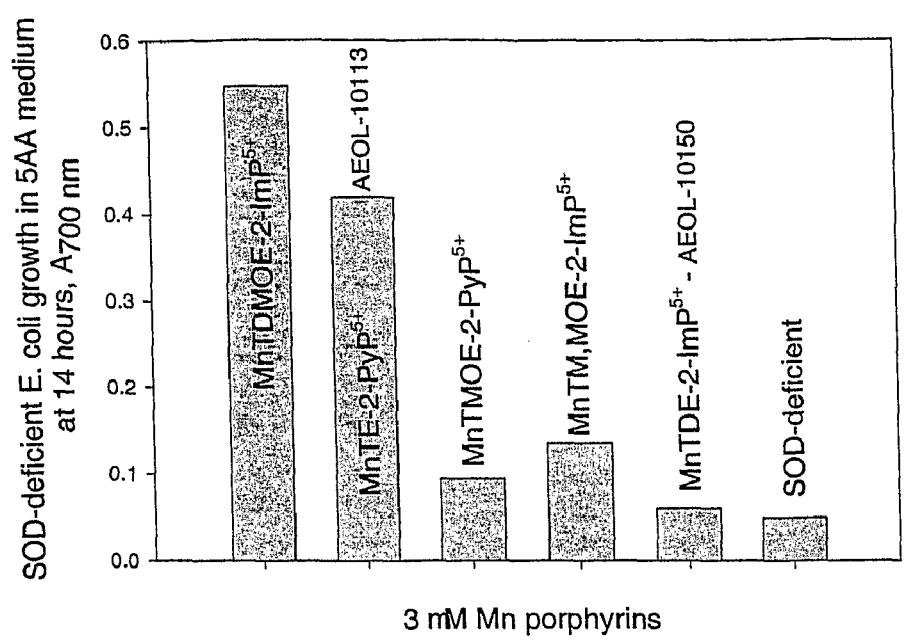
FIG. 10. Aerobic growth of SOD-deficient *E. coli* in 5AA minimal medium at 14 hours, measured as $A_{700\ nm}$, in the presence of 3 μM Mn(III) methoxyethylpyridyl- and imidazolyl porphyrins.

All three newly synthesized methoxyethylporphyrins have similar SOD-like activity and lipophilicity (Table 1), and are not toxic to E. coli under all conditions tested. Their $k_{cat}$ values are the same in the presence and absence of E. coli cell extract. However, the new compounds differ in their ability to protect E. coli from oxidative stress. At ≦3 µM levels MnT-DMOE-2-ImP$^{5+}$ with highest number of oxygen atoms is the most protective to E. coli among methoxyethyl porphyrins (FIG. 10). It is also more protective than MnTE-2-PyP$^{5+}$, while MnTDE-2-ImP$^{5+}$ is the least effective. While MnTD-MOE-2-ImP$^{5+}$ and MnDTE-2-ImP$^{5+}$ have very similar $k_{cat}$, $E_{1/2}$ and $R_f$ (Table 1), the latter lacks oxygens in its structure, and that may be the source of its inefficiency. The data are in accord with a spinal cord study which suggests that MnTDE-2-ImP$^{5+}$ was less effective in passing the spinal cord blood barrier than MnTE-2-PyP$^{5+}$, when both compounds are given intravenously (Sheng et al, Free Radic. Biol. Med. In preparation (2003)).

In summary, it has been shown that the modification of the catalytic antioxidants MnTE-2-PyP$^{5+}$ and MnTDE-2-ImP$^{5+}$, either by increasing the length of the side chains or introducing oxygen atoms, results in compounds, such as MnTnHex (nOct)-2-PyP$^{5+}$ and MnTDMOE-2-ImP$^{5+}$, which can be promising for the treatment of oxidative stress injuries.

The abbreviations used herein are: Mn$^{III/II}$P$^{5+/4+}$ any Mn porphyrin in oxidized and reduced state, MnT(alkyl)-2-PyP$^{5+}$, Mn(III) 5,10,15,20-tetrakis(N-alkylpyridinium-2-yl) porphyrin; alkyl being methyl (M), ethyl (E), n-propyl (nPr), n-butyl (nBu), n-hexyl (nHex) and n-octyl (nOct). MnTDE-2-ImP$^{5+}$, Mn(III) 5,10,15,20-tetrakis[N,N'-diethylimidazo-lium-2-yl]porphyrin, this porphyrin has previously (Sheng et al, Drug News and Perspectives 15:654-665 (2002)) and elsewhere) been erroneously abbreviated as MnTDE-1,3-ImP$^{5+}$, whereby 1 and 3 were indicating the imidazolyl nitrogens, rather than the position 2 where the imidazolyl is attached to the porphyrin ring; MnTMOE-2-PyP$^{5+}$ (MOE), Mn(III) tetrakis 5,10,15,20-tetrakis[N-(2-methoxyethyl)pyridinium-2-yl]porphyrin; MnTM,MOE-2-ImP$^{5+}$ (M,MOE), Mn(III) tetrakis 5,10,15,20-tetrakis[N-methyl-N'—(2-methoxyethyl) imidazolium-2-yl]porphyrin; MnTDMOE-2-ImP$^{5+}$ (DMOE), Mn(III) tetrakis 5,10,15,20-tetrakis[N,N'-di(2-methoxyethyl)imidazolium-2-yl]porphyrin; NHE, normal hydrogen electrode; SOD, superoxide dismutase; ROS and RNS reactive oxygen and nitrogen species. SOD-deficient, ΔsodA/ΔsodB, JI132 E. coli; SOD-proficient wild type, AB1157 E. coli; 5AA, 5 amino acids; M9CA, M9 casamino acids medium; LB, Luria-Bertani Medium; NHE, normal hydrogen electrode. The porphyrin having Mn in its +3 state is assigned as a neutral species.

The entire content of all documents cited herein are incorporated herein by reference, as is: Improving bioavailability of SOD mimics. Comparison of new Mn(III) methoxyethylpyridyl- and imidazolylporphyrins with Mn(III) N-alkylpyridylporphyrins in complementing SOD-deficient E. coli by Ines Batinic-Haberle, Ayako Okado-Matsumoto, Ivan Spasojevic, Robert D. Stevens, Peter Hambright, Pedatsur Neta, Irwin Fridovich, J. Biol. Chem. Submitted.

TABLES

TABLE 1

Metal-centered redox potentials $E_{1/2}$, log $k_{cat}$ for O$_2$ dismutation and chromatographic $R_f$ values for Mn(III) porphyrins.

| Porphyrin | $E_{1/2}$, mV vs NHE[a] | log $k_{cat}$[b] | $R_f$[c] |
|---|---|---|---|
| MnTMOE-2-PyP$^{5+}$ | +251 | 8.04 | 0.16(0.18) |
| MnTM,MOE-2-ImP$^{5+}$ | +356 | 7.98 | 0.15(0.17) |
| MnTDMOE-2-ImP$^{5+}$ | +365 | 7.59 | 0.21(0.24) |
| MnTDE-2-ImP$^{5+}$ | +346 | 7.83 | 0.17(0.23) |
| MnTM-2-PyP$^{5+d}$ | +220 | 7.79 | 0.09(0.13) |
| MnTE-2-PyP$^{5+d}$ | +228 | 7.73[e] | 0.13(0.21) |
| MnTnPr-2-PyP$^{5+d}$ | +238 | 7.38 | 0.20(0.31) |
| MnTnBu-2-PyP$^{5+d}$ | +254 | 7.25 | 0.33(0.46) |
| MnTnHex-2-PyP$^{5+d}$ | +314 | 7.48 | 0.57(0.63) |
| MnTnOct-2-PyP$^{5+d}$ | +367 | 7.71 | 0.08(0.86) |

[a]$E_{1/2}$ (±3 mV) determined in 0.1 M NaCl, 0.05 M phosphate buffer, pH 7.8.
[b]$k_{cat}$ (±30%) determined by pulse radiolysis, pH 7.8, (22 ± 1) ° C.;
[c]$R_f$, compound path/solvent path on silica gel TLC plates in KNO$_3$-saturated H$_2$O/H$_2$O/acetonitrile = 1/1/8, $R_f$ for metal-free porphyrins are in parenthesis.
[d]Data from Batinic-Haberle et al, , J. Chem. Soc., Dalton Trans., pgs. 2689-2696 (2002).
[e]Data from Batinic-Haberle et al, Inorg. Chem. 40: 726 (2001).

TABLE 2

Molar absorptivities of methoxyethyl porphyrins, $H_2TDE$-2-$ImP^{5+}$ and their Mn complexes.

| Porphyrin | $\lambda_{max}$ (log ε)[a] |
|---|---|
| $H_2TMOE$-2-$PyP^{4+}$ | 416(5.44), 512.5(4.34), 545(3.68), 584(3.93), 636.5(3.46) |
| $H_2TDE$-2-$ImP^{4+}$ | 407(5.26), 507(4.23), 541(3.83), 578.5(3.87), 630(3.87) |
| $H_2TM,MOE$-2-$ImP^{4+}$ | 408.5(5.27), 507.5(4.26), 541(3.87), 580(3.90), 632.5(3.89) |
| $H_2TDMOE$-2-$ImP^{4+}$ | 411(5.22), 509.5(4.19) 542.5(3.82), 581(3.83), 634(3.86) |
| $MnTMOE$-2-$PyP5^{5+}$ | 364.5(4.75), 413(4.41), 455(5.24), 500(3.84), 558.5(4.16), 785(3.34) |
| $MnTDE$-2-$ImP^{5+}$ | 348.5(4.66), 446(5.08), 505.5(3.77), 553(4.06), 588(3.95), 795(3.34) |
| $MnTM,MOE$-2-$ImP^{5+}$ | 349(4.73), 412.5(4.53), 447.5(5.14), 503.5(3.80), 553.5(4.13), 588(4.04), 799(3.34) |
| $MnTDMOE$-2-$ImP^{5+}$ | 350(4.67), 4.14(4.48), 448.5(5.09), 503(3.74), 555(4.08), 590(4.02), 803.5(3.33) |

[a] Molar absorptivities were determined in water at room temperature.

TABLE 3

ESMS of methoxyethylporphyrins and their alkyl analogues.[a]

| Porphyrin | $E_{PyP}$[b] | $nBu$[b] | $MOE_{PyP}$ | m/z $DE_{ImP}$ | $M,MOE_{ImP}$ | $DMO_{ImP}$ |
|---|---|---|---|---|---|---|
| $H_2P^{4+}/4$ | 184 | 212 | 214 | 201 | 217 | 261 |
| $H_2P^{4+}$ + AN/4 | 194 | 222 | 224 | 211 | 227 | |
| $H_2P^{4+}$—$H^+/3$ | 245 | 282 | 285 | 267 | 289 | 347 |
| $H_2P^{4+}$—$H^+$ + AN/3 | 258 | | | | | |
| $H_2P^{4+}$-$a^+$-$H^+$ + $CH_3^+/3$ | | | 270 | | 274 | 333 |
| $H_2P^{4+}$-$a^+/3$ | 235 | 263 | 265 | 258 | 269 | 328 |
| $H_2P^{4+}$-$a^+$-$H^+/2$ | 352 | 394 | 398 | 386[c] | 403[c] | 491[c] |
| $H_2P^{4+}$-$2a^+/2$ | | 366[c] | 368 | 372[c] | 374[c] | 462[c] |
| $H_2P^{4+}$-$2a^+$ + $H^+/3$ | | | | 249[c] | | |
| $H_2P^{4+}$-$a^+$-$a$-$2H^+$ | | | | 743[c] | | |
| $H_2P^{4+}$-$3a^+$ | | | 677 | | | |
| $H_2P^{4+}$-$3a^+$+$H^+/2$ | | | | 239[c] | | |
| $H_2P^{4+}$-$a^+$ + $CH_3^+/4$ | | | | 203 | 206 | 250 |
| $H_2P^{4+}$-$2a^+$ + $CH_3^+/3$ | | | 251[c] | | 255 | 313 |
| $H_2P^{4+}$-$2a^+$ + $2CH_3^+/4$ | | | 192 | | 195 | 239 |
| $H_2P^{4+}$-$3a^+$ + $CH_3^+/2$ | | | 346[c] | | 352[c] | |
| $H_2P^{4+}$-$3a^+$ + $2CH_3^+/3$ | | | 236 | | | |
| $H_2P^{4+}$-$3a^+$ + $2CH_3^+$-$H^+/2$ | | | 324[c] | | | |
| $H_2P^{4+}$-$4a^+$ + $CH_3^+$ | | | 633[c] | | | |
| $H_2P^{4+}$-$2H^+/2$ | 367 | 423 | 426 | 400 | 432 | 520[c] |
| $H_2P^{4+}$—$H^+$ + $Cl^-/2$ | | | | 418 | 450 | |

[a] ~0.5 mM solutions of porphyrins in 1:1 = acetonitrile:$H_2O$, 20 V cone voltage, a is either alkyl or methoxyethyl group.
[b] Batinic-Haberle et al, , J. Chem. Soc., Dalton Trans., pgs. 2689-2696 (2002).
[c] 30 V cone voltage. The fission of $CH_2$—O—$CH_3$ radical from methoxyethyl group is noted for simplicity as the loss of methoxyethyl ($a^+$) and the gain of $CH_3^+$.

TABLE 4

ESMS of Mn(III) methoxyethylporphyrins, and their alkyl analogues.[a]

| | m/z | | | | | |
|---|---|---|---|---|---|---|
| Porphyrins | $E_{PyP}$[b] | $nBu$[b] | $MOE_{PyP}$ | $DE_{ImP}$ | $M,MOE_{ImP}$ | $DMOE_{ImP}$ |
| $Mn^{III}P^{5+}/5$ | 157 | | 181 | 171 | 184 | 219 |
| $Mn^{III}P^{5+}$ + AN/5 | 166 | 188 | 190 | 179 | 193 | 227 |
| $Mn^{III}P^{5+}$ + 2AN/5 | 174 | 196 | 198 | 187 | 201 | 236 |
| $Mn^{III}P^{5+}$ + 3AN/5 | 182 | 205 | 206 | 195 | 209 | 244 |
| $Mn^{III}P^{5+}$ + 4AN/5 | 190 | 213 | 214 | 204 | | 252 |
| $Mn^{III}P^{5+}$ + 5AN/5 | | | | | | 260 |
| $Mn^{III}P^{5+}$ + $Cl^-/4$ | 206 | 234 | 236 | 223 | 239 | 283 |
| $Mn^{III}P^{5+}$ + $Cl^-$ + AN/4 | 216 | | | | | |
| $Mn^{III}P^{5+}$ + $2Cl^-/3$ | 286 | 323 | 326 | 309 | 330 | 389 |
| $Mn^{III}P^{5+}$-$a^+$ + $Cl^-/3$ | 265 | 293 | 295 | | | 357 |
| $Mn^{III}P^{5+}$-$a^+/4$ | | | 212 | 207 | 215 | 259 |
| $Mn^{III}P^{5+}$-$a^+$ + AN/4 | 200 | 221 | | | | 269 |
| $Mn^{III}P^{5+}$-$2a^+/3$ | 243 | 262 | 263 | 266[c] | 268 | |
| $Mn^{III}P^{5+}$-$2a^+$ + AN/3 | | 276 | 277 | | | |
| $Mn^{III}P^{5+}$-$3a^+/2$ | | | 365 | | 371[b] | |
| $Mn^{III}P^{5+}$-$3a^+$ + $Cl^-$ | | | 765 | | | |
| $Mn^{III}P^{5+}$-$4a^+$ | | | 671 | | | |
| $Mn^{III}P^{5+}$-$a^+$ + $CH_3^+$ + $Cl^-/4$ | | | 225 | | | 272 |

TABLE 4-continued

ESMS of Mn(III) methoxyethylporphyrins, and their alkyl analogues.[a]

| Porphyrins | $E_{PyP}$[b] | nBu[b] | $MOE_{PyP}$ | $DE_{ImP}$ | $M,MOE_{ImP}$ | $DMOE_{ImP}$ |
|---|---|---|---|---|---|---|
| $Mn^{III}P^{5+}$-2a$^+$ + $CH_3^+$ + $Cl^-$/3 | | | 280 | | | |
| $Mn^{III}P^{5+}$-4a$^+$ + $CH_3^+$/2 | | | | | | |
| $Mn^{III}P^{5+}$—$CH_3^+$ + $H^+$/5 | | | | | 181[b] | |
| $Mn^{III}P^{5+}$—$Mn^{3+}$ + $H^+$/3 | | 281 | | | | |
| $Mn^{III}P^{5+}$—$Mn^{3+}$ + 2$H^+$/4 | | | 214 | | 217 | |
| $Mn^{II}P^{4+}$/4 | 197 | | 227 | 214 | | 274 |
| $Mn^{II}P^{4+}$ + AN/4 | 207 | 235 | | 224 | | |
| $Mn^{II}P^{4+}$ + $Cl^-$/3 | 274 | 312 | 314 | 297 | 318 | 377 |
| $Mn^{II}P^{4+}$ + 2$Cl^-$/2 | 428 | | 488 | 462 | 494 | 583 |
| $Mn^{II}P^{4+}$-a$^+$/3 | 253 | 281 | 283[c] | 276[c] | 287 | |
| $Mn^{II}P^{4+}$-2a$^+$/2 | | | | | 401[c] | |
| $Mn^{II}P^{4+}$-2a$^+$ + $H^+$/3 | | | | | | 326 |
| $Mn^{II}P^{4+}$-a$^+$ + $CH_3^+$ + $Cl^-$/3 | | | 299 | | 304 | 362 |
| $Mn^{II}P^{4+}$-4a$^+$ + $CH_3^+$ | | | 687 | | | |
| $Mn^{II}P^{4+}$-7a$^{3+}$ | | | | 653[d] | | |
| $Mn^{II}P^{3+}$/3 or $Mn^{I}P^{3+}$/3 | | 295 | 303 | 285[c] | 307 | 365 |

[a] ~0.5 mM solutions of porphyrins in 1:1 = acetonitrile:$H_2O$, 20 V cone voltage. a is either alkyl or methoxyethyl group.
[b] Batinic-Haberle et al, , J. Chem. Soc., Dalton Trans., pgs. 2689-2696 (2002).
[c] 30 V cone voltage.
[d] signal of very low intensity. The fission of $CH_2$—O—$CH_3$ radical from methoxyethyl group is noted for simplicity as the loss of methoxyethyl (a$^+$) and the gain of $CH_3^+$.

What is claimed is:

1. A compound of the formula:

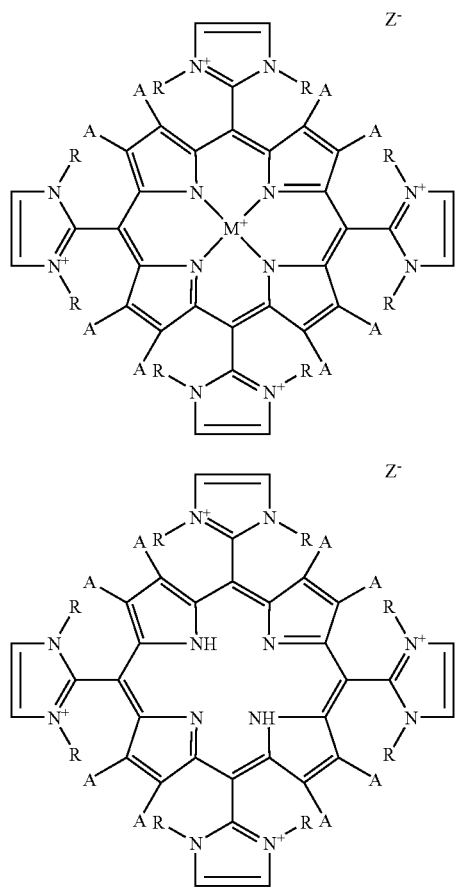

VII

VIII wherein at least one R on each imidazole ring is, independently, —$(CH_2)_mCH_2OX$ or —$(CH_2CH_2O)_nX$, the other R being, independently, a $C_2$-$C_{12}$alkyl, (straight chain or branched), wherein m is 1-6, n is 3-50, X is $C_2$-$C_{12}$alkyl, (straight chain or branched), each A is, independently, hydrogen or an electron withdrawing group, M is metal selected from the group consisting of manganese, iron, copper, cobalt, nickel and zinc, and $Z^-$ is a counterion.

2. The compound according to claim 1 wherein at least one A is halogen, $NO_2$ or CHO.

3. The compound according to claim 1 wherein said compound is of Formula VII.

4. The compound according to claim 3, wherein at least one A is halogen.

5. The compound according to claim 3, wherein at least one A is $NO_2$.

6. The compound according to claim 3, wherein at least one A is CHO.

7. The compound according to claim 1 wherein said compound is of Formula VIII.

8. The compound according to claim 7, wherein at least one A is halogen.

9. The compound according to claim 7, wherein at least one A is $NO_2$.

10. The compound according to claim 7, wherein at least one A is CHO.

* * * * *